(12) United States Patent
Olson et al.

(10) Patent No.: US 10,456,531 B2
(45) Date of Patent: *Oct. 29, 2019

(54) INJECTION DEVICE

(71) Applicant: SHL Group AB, Nacka Strand (SE)

(72) Inventors: Stephan Olson, Danderyd (SE); Lennart Brunnberg, Tyreso (SE)

(73) Assignee: SHL Group AB, Zug (CH)

(*) Notice: Subject to any disclaimer, the term of this patent is extended or adjusted under 35 U.S.C. 154(b) by 122 days.

This patent is subject to a terminal disclaimer.

(21) Appl. No.: 15/684,451

(22) Filed: Aug. 23, 2017

(65) Prior Publication Data

US 2018/0008784 A1 Jan. 11, 2018

Related U.S. Application Data

(63) Continuation of application No. 15/220,478, filed on Jul. 27, 2016, which is a continuation of application
(Continued)

(30) Foreign Application Priority Data

Oct. 25, 2005 (SE) ...................................... 0502370

(51) Int. Cl.
*A61M 5/315* (2006.01)
*A61M 5/31* (2006.01)
(Continued)

(52) U.S. Cl.
CPC .......... *A61M 5/31586* (2013.01); *A61M 5/19* (2013.01); *A61M 5/2033* (2013.01);
(Continued)

(58) Field of Classification Search
CPC ............ A61M 5/31548; A61M 5/3155; A61M 5/31551; A61M 5/31553
See application file for complete search history.

(56) References Cited

U.S. PATENT DOCUMENTS 5,320,609 A * 6/1994 Haber ................. A61M 5/2033
604/135
5,573,513 A * 11/1996 Wozencroft ........ A61M 5/3257
128/919
(Continued)

FOREIGN PATENT DOCUMENTS

EP 0298067 A1 1/1989
WO 2004028598 A1 8/2004
(Continued)

OTHER PUBLICATIONS

PCT International Search Report issued in International Application No. PCT/SE2005/001764 dated Feb. 28, 2006.
(Continued)

*Primary Examiner* — Matthew F Desanto
(74) *Attorney, Agent, or Firm* — McDonnell Boehnen Hulbert & Berghoff LLP

(57) ABSTRACT

Injection device comprising a tubular elongated main body, a needle shield slidably arranged in said main body, a needle shield link slidably connected to said needle shield, a cartridge containing medicament arranged in said main body, a needle connected to said cartridge, a plunger operatively arranged to said cartridge for ejecting said medicament through said needle and arranged on its upper part with a number of outwardly extending stop members, spring means arranged to said plunger for operating said plunger, a dose activating means, a needle shield spring surrounding the needle shield link. The injection device is capable of setting and delivering a certain preset dose.

18 Claims, 26 Drawing Sheets

Related U.S. Application Data

No. 15/141,213, filed on Apr. 28, 2016, which is a continuation of application No. 12/574,080, filed on Oct. 6, 2009, now Pat. No. 9,408,976, which is a continuation of application No. 10/597,384, filed as application No. PCT/SE2005/001764 on Nov. 24, 2005, now Pat. No. 7,597,685.

(60) Provisional application No. 60/630,197, filed on Nov. 24, 2004.

(51) Int. Cl.
    *A61M 5/20*     (2006.01)
    *A61M 5/32*     (2006.01)
    *A61M 5/19*     (2006.01)
    *A61M 15/00*     (2006.01)
    *A61M 5/24*     (2006.01)

(52) U.S. Cl.
CPC ...... *A61M 5/3146* (2013.01); *A61M 5/31505* (2013.01); *A61M 5/31525* (2013.01); *A61M 5/31553* (2013.01); *A61M 5/3202* (2013.01); *A61M 5/3257* (2013.01); *A61M 5/3272* (2013.01); *A61M 15/0066* (2014.02); *A61M 5/24* (2013.01); *A61M 5/3156* (2013.01); *A61M 5/31563* (2013.01); *A61M 2005/2013* (2013.01)

(56) References Cited

U.S. PATENT DOCUMENTS

| | | | |
|---|---|---|---|
| 5,658,259 | A | 8/1997 | Pearson et al. |
| 5,679,111 | A | 10/1997 | Hjertman et al. |
| 6,290,679 | B1 | 9/2001 | Hostettler et al. |
| 7,597,685 | B2 * | 10/2009 | Olson ............... A61M 5/2033 604/208 |
| 9,408,976 | B2 * | 8/2016 | Olson ............... A61M 5/2033 |
| 2006/0270984 | A1 | 11/2006 | Hommann |

FOREIGN PATENT DOCUMENTS

| | | |
|---|---|---|
| WO | 2005044345 A1 | 5/2005 |
| WO | 2005044348 A1 | 5/2005 |

OTHER PUBLICATIONS

PCT International Preliminary Exam Report on Patentability issued in International Application No. PCT/SE2005/001754 dated May 30, 2007.

* cited by examiner

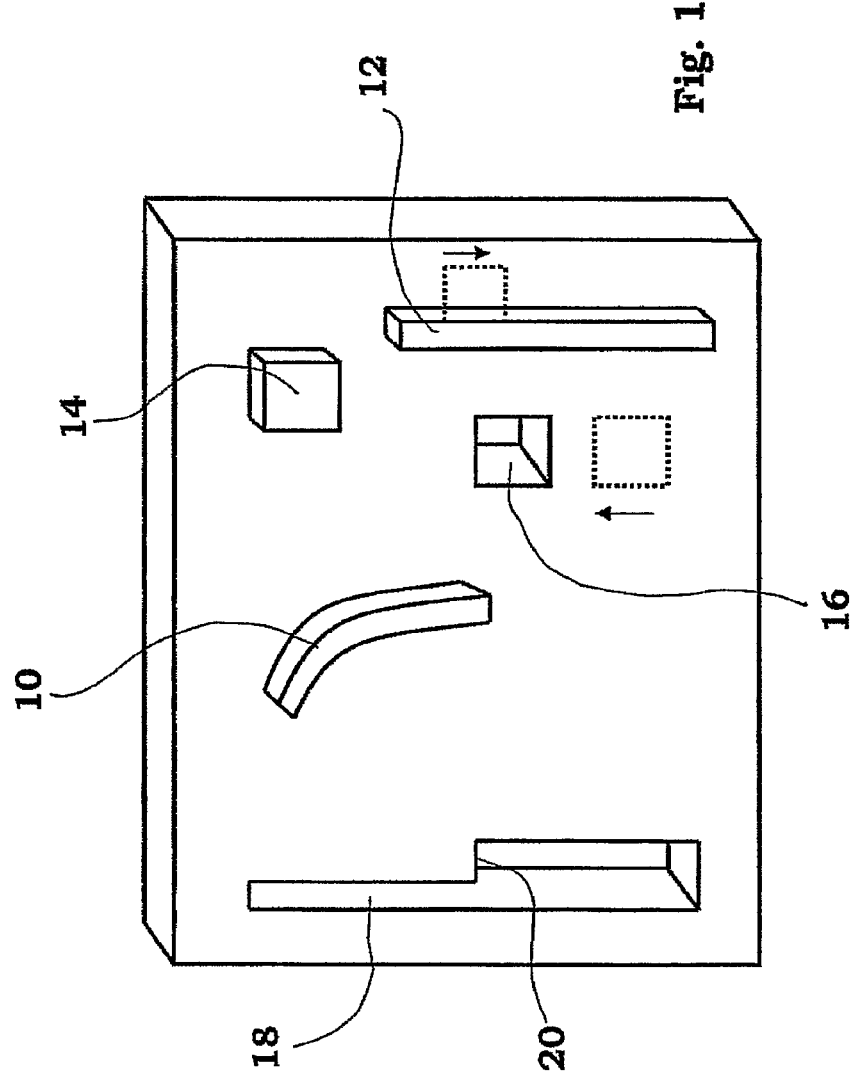

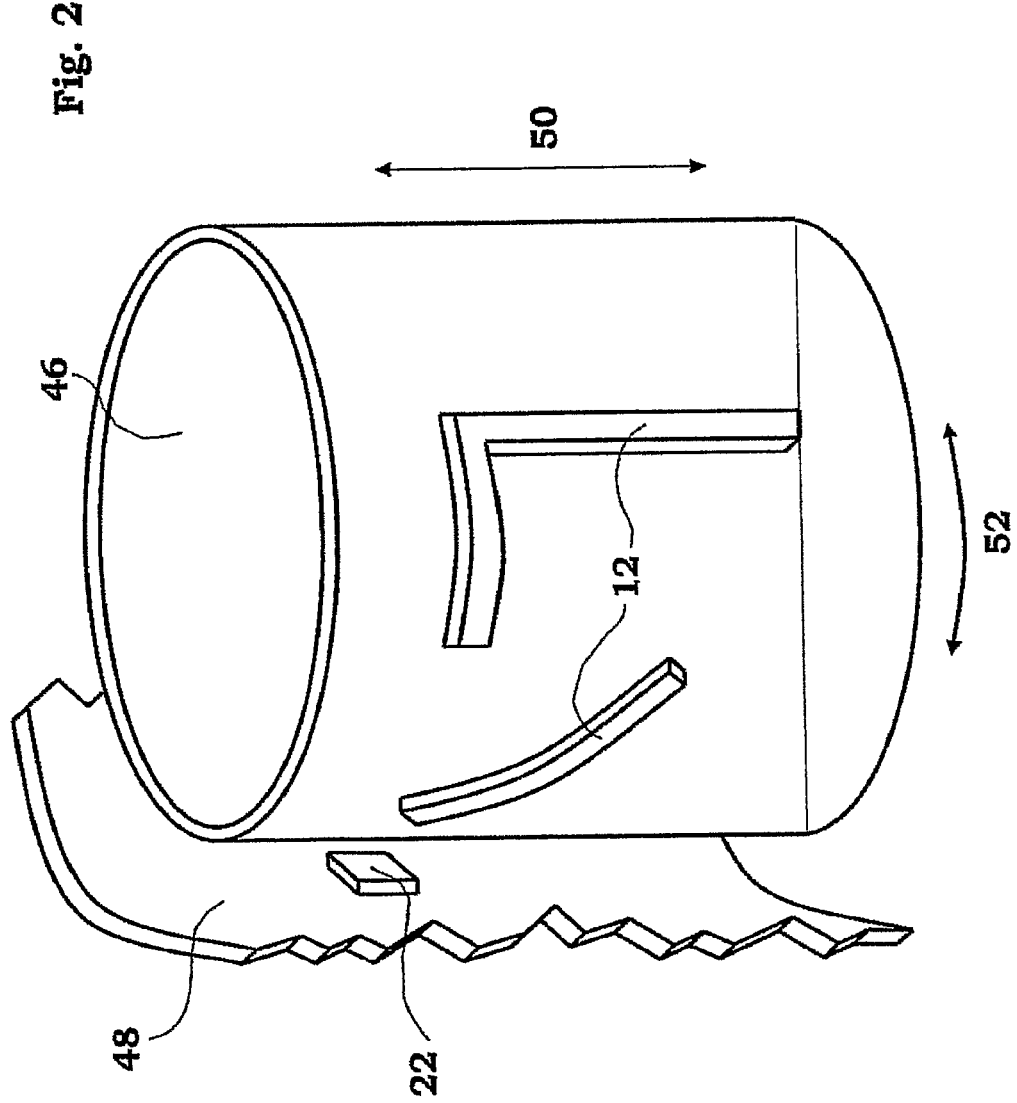

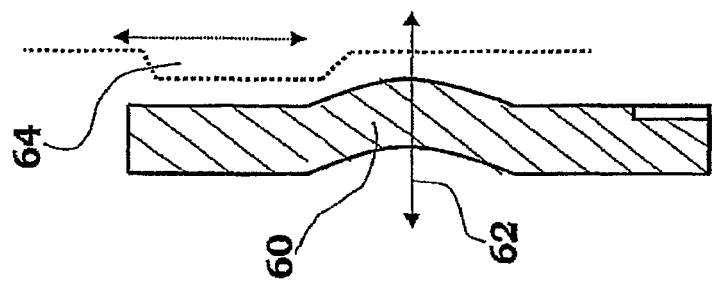
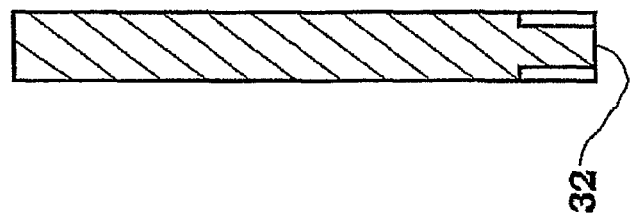
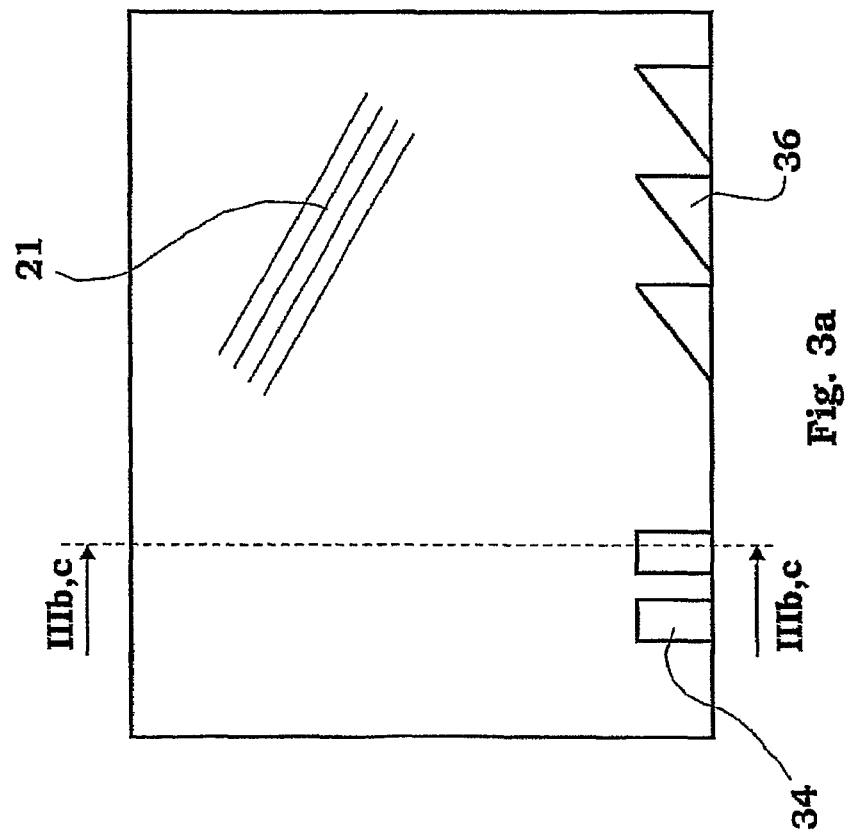

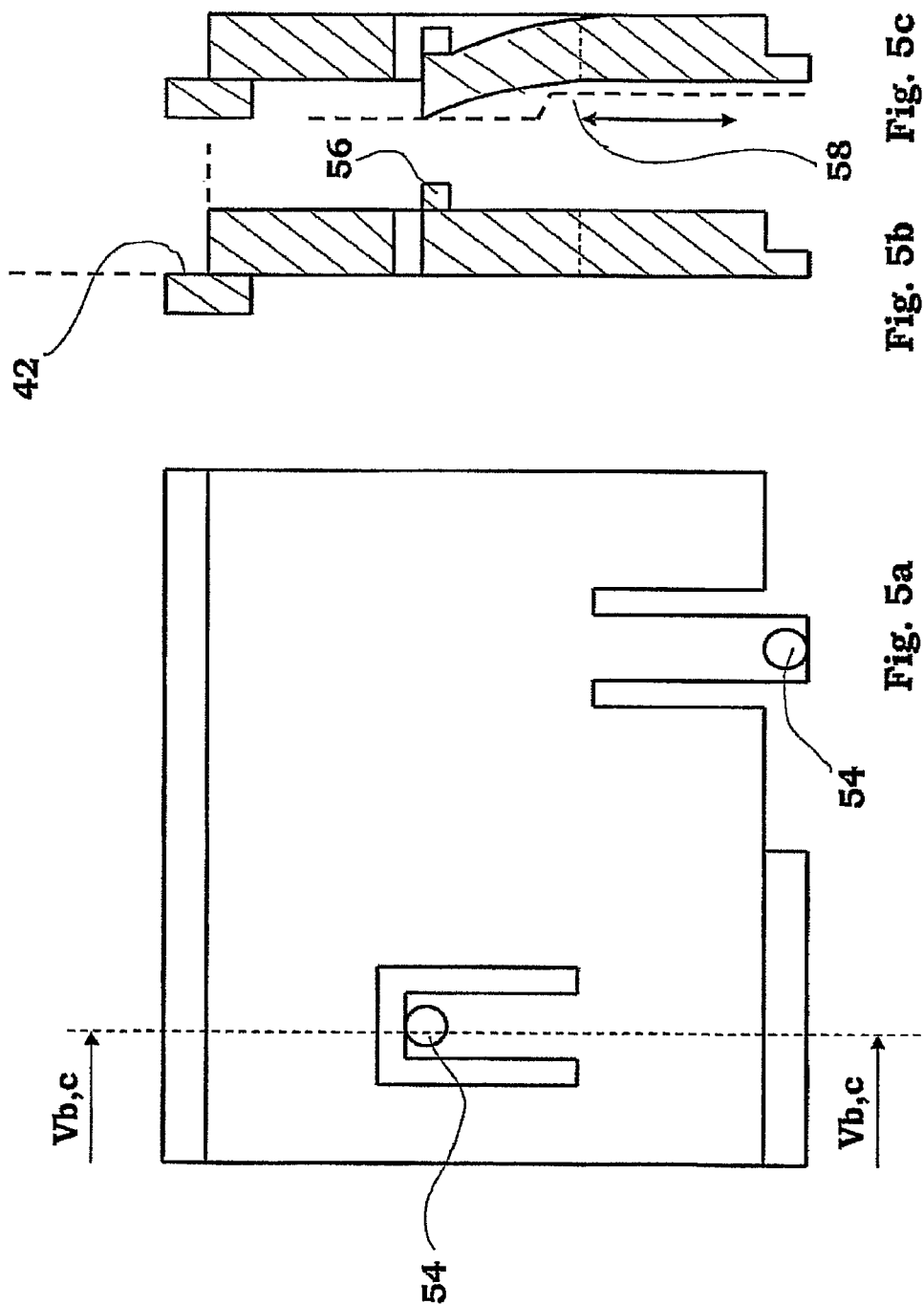

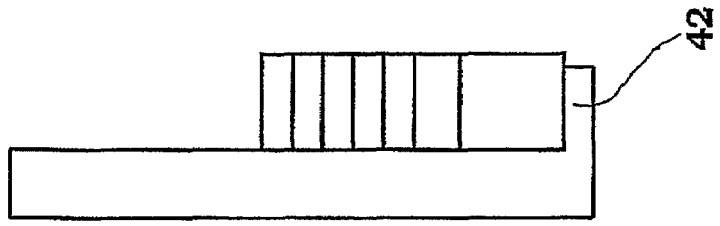
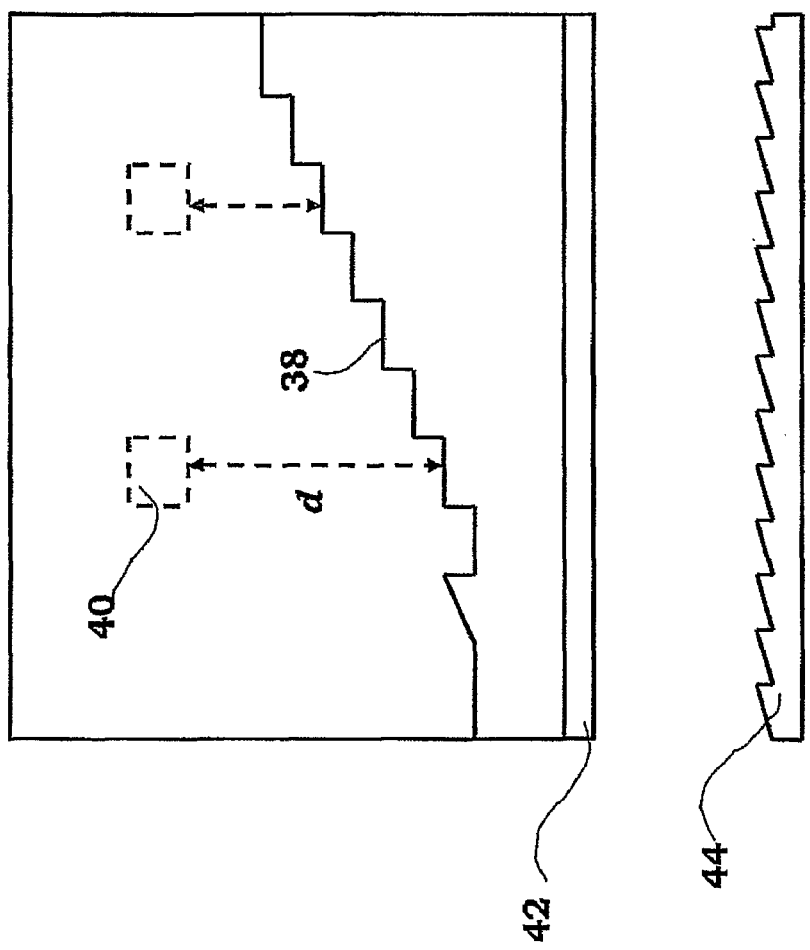

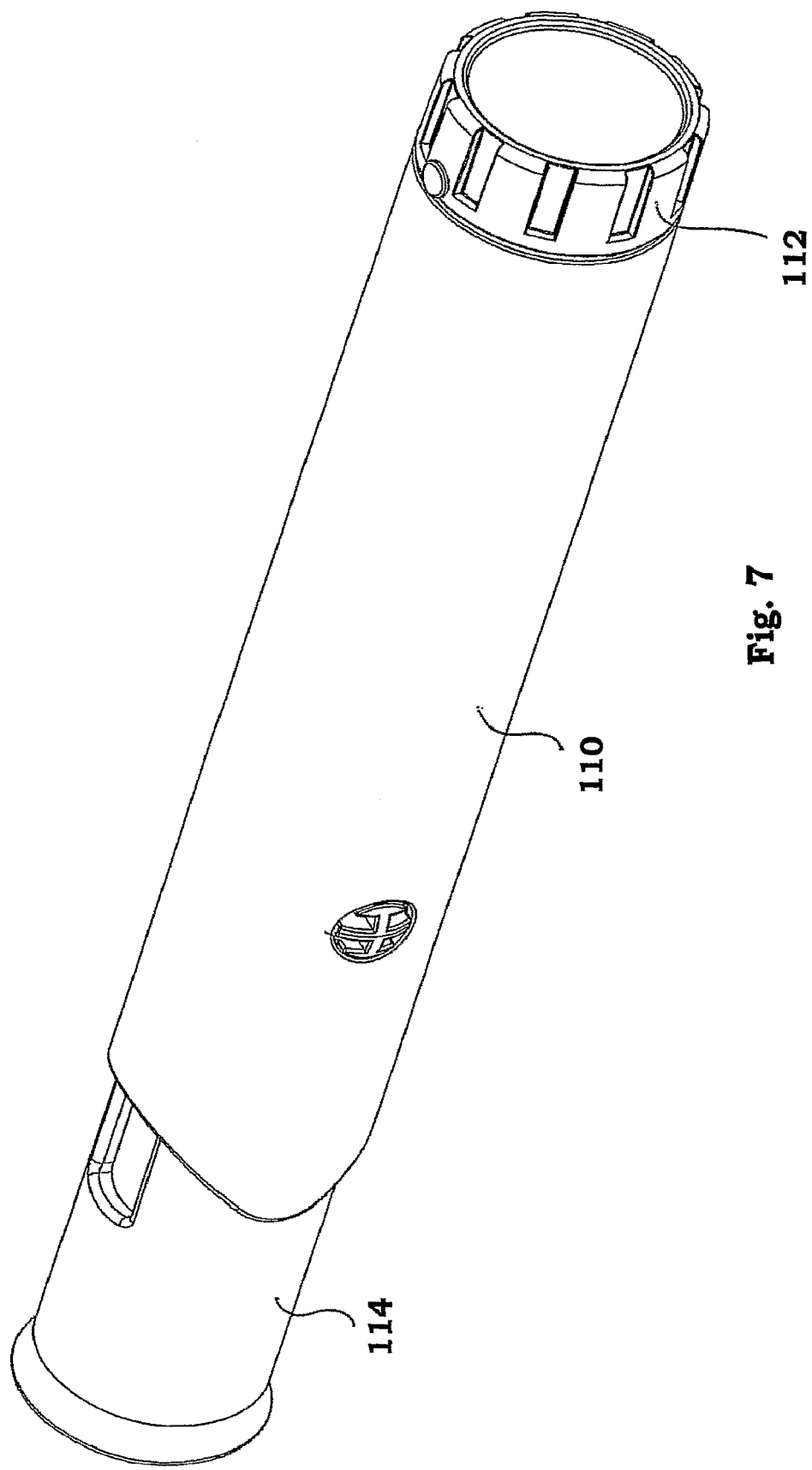

INJECTION DEVICE

CROSS REFERENCE TO RELATED APPLICATIONS

The present application is a continuation application of U.S. patent application Ser. No. 15/220,478 filed Jul. 27, 2016 which is a continuation application of U.S. patent application Ser. No. 15/141,213 filed Apr. 28, 2016 which is a continuation application of U.S. patent application Ser. No. 12/574,080, filed Oct. 6, 2009, now U.S. Pat. No. 9,408,976, which is also a continuation application of U.S. patent application Ser. No. 10/597,384, filed Jun. 24, 2008, now U.S. Pat. No. 7,597,685, which is a 371 of International Patent Application No. PCT/SE05/01764, filed Nov. 24, 2005 which claims the benefit of U.S. Provisional Patent Application No. 60/630,197, filed Nov. 24, 2004 and Swedish Patent Application No 0502370.0, filed Oct. 25, 2005 and the entire contents of which are incorporated entirely herein by reference.

TECHNICAL AREA

The present invention relates to delivery devices such as injectors, mouth or nasal inhalers, powder or aerosol inhalers, nebulizers and the like.

TECHNICAL BACKGROUND

There are on the market a number of different delivery devices with varying degrees of automatic functions. The general trend is also that patients should be able to administer drugs and medicament by themselves, i.e. without the need for trained staff to administer the drugs.

There are however a number of aspects regarding delivery devices that are to be used by non-trained persons both in view of safety, both for the user and others that may come in contact with the device, as well as in view of handling and operation.

For safety reasons many devices have been arranged with cover or protection means that are manually or automatically activated in order to protect persons from for example an injection needle, in particular after use.

Many devices are provided with enclosures such as cartridges, ampoules or syringes containing medicament in liquid form. When filling these containers with liquid a small amount of air is very often entrapped in the container, which air has to be removed before delivery. Some devices are of multi-chamber type where one component is powder and the other is liquid or two liquids or more liquids and powder chambers.

For some types of medicament enclosures and treatment schemes there is a need to deliver a precise dose, which may be less than the total amount in the enclosure. For some types of medicament the dose to be delivered is so small that it is not practically possible to provide such a small compartment in the enclosure or to provide a device that is capable of expelling the content from such a small compartment.

The above mentioned functions have been realised in a number of delivery devices with a varying degree of complexity.

European patent application No. 298 067 discloses an injection device where mixing of two components in a cartridge and the subsequent de-aeration is performed by screwing an upper and a lower part of the device. This solution requires quite a lot of manual handling by the user in order to get the device ready for injection.

EP 298 067 further discloses a dose setting feature of the device, however without any specifications regarding the manner this can be performed.

Regarding needle covers that protect the needle after use, there are many documents disclosing this feature, e.g. U.S. Pat. No. 5,658,259 and EP 298 067. The majority of these devices include either rather complex mechanisms, like the former document, that makes the production of the device rather costly or manually handled needle covers, like the latter document, with the risk that the person handling the device un-intentionally injures himself on the needle.

There is thus a need for a device that is easy to handle, fulfills the safety requirements that are requested for these types of devices and is uncomplicated and can be manufactured at a reduced cost.

BRIEF DESCRIPTION OF THE INVENTION

The aim of the present invention is to provide a delivery device that is easy and safe to handle, based on a method for designing various features and various combinations.

This aim is fulfilled with a delivery device according to claim 1. Further advantageous features of the present invention are the object of the dependent claims.

According to a main aspect of the invention it is characterised by a device for controlling and performing functions of a device for delivery of medicament, comprising a number of components arranged to co-act with each other, comprising co-operating means, at least some of them arranged on the surfaces of the components, comprising guide means capable of guiding the relative movement between two co-acting components for controlling and performing at least one function.

According to a further aspect of the invention the guide means comprises mechanical members like ridges, ledges or groove having side surfaces arranged on one component, against which protrusions, ridges, ledges or grooves on another component are in contact for guiding the relative movement.

According to yet an aspect of the invention the co-operating means further comprises locking means capable of locking the co-acting components relative each other at pre-defined mutual positions.

According to another aspect of the invention the locking means comprises grooves, cut-outs, recesses protrusions on one component, co-operating with protrusions, ridges, ledges or recesses on another component for locking the movement between the co-acting components.

According to a further aspect of the invention the co-operating means comprises holding means, capable of holding two co-acting components in mutual positions in a first direction until one or more of other components are moved a certain amount in a direction deviating from said first direction, wherein the co-acting components are released from each other.

Further the holding means comprises ledges, ridges, recesses on one component, co-acting with protrusions, ledges ridges or recesses on another component.

Preferably at least one component is arranged as a generally tubular member, the inner and/or outer surfaces of which are arranged with said co-operating means.

With the principle of the invention there are a number of advantages that are obtained. By utilizing co-operating means on at least two, preferably more, co-acting components for guiding their relative movement, the interaction between the components can be simplified, especially in view of designing and manufacturing the device and still have a reliable function. Further the co-operating means can be formed as locking members capable of locking the co-acting components. Further the co-operating means can be designed to hold the components in pre-defined positions relative each other.

The co-operating means are preferably mechanical members in the form of grooves, ledger ridges, recesses, cut-outs, protrusions, threads and the like that are designed to guide, lock and/or hold the co-acting components in their movement relative each other.

For certain types of applications such as injectors having a generally tubular form, at least one of the components is preferably tubular, having co-operating means arranged on its surfaces, which could be inner, outer and edge surfaces. The possibilities with the principle according to the invention are numerous since the number of surfaces that are available and the types and design of co-operating means possible are vast, almost all types of movements and functions are feasible, with a reduced number of components for the device compared to the state of the art.

This could be achieved without reducing the overall functionality of the device. Rather on the contrary, since fewer components generally are needed for performing a number of functions, the interplay between components, and thus the dependency that each component in a chain or series is designed so that the desired function is obtained, is reduced.

In all a device with a freedom to design and create a high degree of robust functionality is obtained with a reduced number of components, whereby the manufacturing costs are kept at a low level, which in turn enables the device to be used for example in a single dose delivery device that is discarded after completed injection.

These and other aspects of and advantages with the present invention will become apparent from the following detailed description and the accompanying drawings.

BRIEF DESCRIPTION OF THE DRAWINGS

In the detailed description, reference will be made to the accompanying drawings, of which FIG. 1 is a schematic view of the general principle of the present invention, FIG. 2 is a variant of the general principle including a cylindrical component, a rotator, FIGS. 3a-3c, 4a-4b, 5a-5c and 6a-6c show further variants of the general principle, FIG. 7 is a side view of a first embodiment of an injector comprising the present invention, FIG. 20 is an exploded view of the embodiment according to FIGS. 14-19, and FIG. 21 is a variant of a component comprised in the second embodiment.

DETAILED DESCRIPTION OF THE INVENTION

The general aspect of the invention will first be described in connection to the drawings, FIGS. 1-6.

The novel feature of the invention is the manner of controlling different functions of a device such as an injecting device. Depending on the degree of automation, such devices may have several functions included, which functions are more or less automated and may be working in series or in parallel with each other.

These functions may include priming of the medicament in liquid form prior to injection, mixing of medicament for multi-compartment ampoules or syringes, penetration of a needle into the body of a patient, injection of the medicament in the body of the patient, withdrawal of needle after injection, advancing of a needle shield for protection of the needle and subsequent locking of the needle shield. Further features may include setting of specific doses, delivery of specific doses, etc. The different features and functions entail co-operation and/co-action between different components of the device such as pistons, sleeves, springs, locking hooks, threaded parts and the like.

Figure 4B:
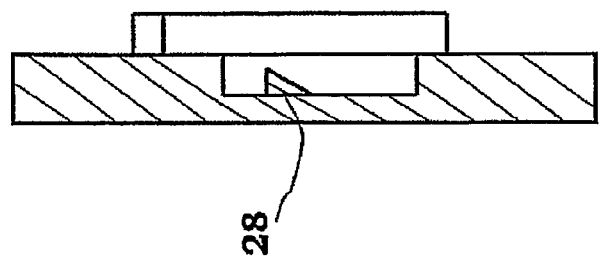
Figure 4A:
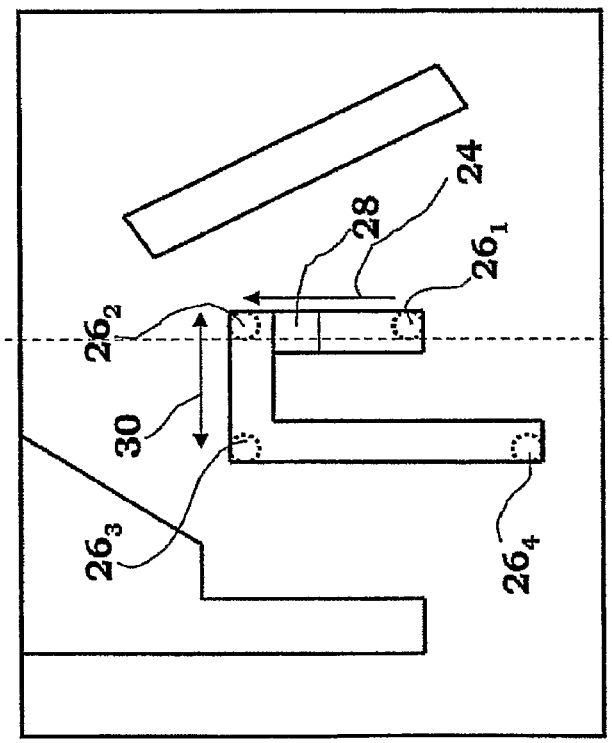

According to the present invention many or all of the above features and functions may be performed and controlled by co-operating means arranged on co-acting components of the device for enabling these functions. The co-operating means comprise mechanical members like cams 10, ridges 12, protrusions 14, recesses 16, slots and grooves 18, ledges 20, FIG. 1, threads 21, FIG. 3a, and the like, arranged on one or several surfaces of these components. These mechanical members arranged on one component co-operate with mechanical members 22 on another component, which components are arranged to co-act with each other in order to perform a certain function, FIG. 2. The co-operating means could be used to guide a movement between two co-acting components, like is shown in FIG. 4a. First the groove 18 only allows movement in one direction, 24, until a protrusion or pin 26 of the other component has moved from an initial position $26_1$ to a certain position $26_2$. The protrusion may be flexible and the groove may be arranged with a ramp 28, whereby, when the protrusion has passed the ramp, it cannot move back to the initial position. The groove now allows a movement in the direction of the arrow 30 until the protrusion has moved to a position $26_3$ when it is allowed to again move in the direction parallel to the first direction 24 to a position $26_4$.

Not only can the co-operating means be arranged on a surface, but it is also possible to arrange them on edge parts 32, FIGS. 3a-c of the co-acting components. They can be formed as slots that have either straight walls 34 or ramped walls 36 in relation to the direction of the edge. They may further be arranged on one side only, FIG. 3c, or on both sides, FIG. 3b, in the latter case if there are more than two co-operating components. The edge parts can be formed step-like 38 as shown in FIG. 6a for providing certain defined distances d that a member 40 on another component is able to move, e.g, for delivering specific doses of medicament.

There could also be formed ledges 42, FIGS. 5 and 6, on the edges of one co-acting component co-operating with another component to form a mutual fixed relationship between the two, FIG. 6a-c. The ledge can either be smooth or be ratchet-like 44 enabling movement in only one direction, FIG. 6c.

The mechanical members can then co-operate to move components 46, 48 relative each other in a controlled manner following a certain pattern of movement, such as slidable movement 50, rotational movement 52 or combinations of these. The mechanical members can further co-operate to lock the components mutually in pre-defined positions after or before a function has been performed and/or hold the components in mutual positions until one or more of the components are moved a certain distance or rotated, after which they are released from each other and a certain function is performed of the device. FIGS. 5a-c show a few variants on movable, resilient locking members 54. The locking member shown in FIG. 5b snaps into a groove or a recess when the pin 56 of the locking member is in a certain position. The locking member shown in FIG. 5c locks into a groove or recess when the co-operating component has moved to a certain position where another component or member 58 acts on the rear side of the locking member. This could then mean a temporary locking because when or if the other component is moved out of contact with the rear side of the locking member, it is moved out of the recess or groove. FIG. 3c shows another type of member 60 that is resiliently flexible in the direction of the arrow 62. When this member is moved to a certain position it comes in contact with a protrusion 64 or the like whereby a frictional contact is obtained. This could be for temporarily holding the two co-acting components or to slow down the movement between the components.

Regarding injecting devices it is preferred that one central part containing these mechanical members is mainly cylindrical, 46, FIG. 2, since the injecting devices generally have this cylindrical "pen"-shape. This cylindrical part 46, hereafter named rotator, is arranged with mechanical members 12 on its surface, which could both the internal and external surface. The rotator could be arranged to be turnable 52 around its centre axis as well as slidable 50 along its centre axis.

The mechanical members of the rotator co-operate with other parts, 48, partly shown in FIG. 2, of the device, which parts are also arranged with mechanical members 22. As an example, the rotator may be arranged with an inclined ridge or guide, on which another mechanical member of another part is arranged to slide along. This sliding action may cause either the rotator or the other part, or both, to turn. The turning action may for example be to set a dose, to free a third part of the device arranged with a protrusion that is held by a stop ledge that has a certain extension, whereby the turning action causes the protrusion to move past the stop ledge. As an example, the protrusion may be arranged on a part of the device that acts on the syringe or ampoule containing medicament, such as a spring-loaded plunger, and when the protrusion has been moved past the stop ledge, which movement may have been caused by the needle shield pushed into the device, the plunger is free to act on the content of the syringe and thus to inject a dose of medicament.

The rotator or other parts of the device may further be arranged with recesses positioned on its surfaces, into which protrusions or the like will be positioned depending on the movement between the parts. As an example, a protrusion arranged on the needle shield may be moved, as the needle shield is extended to cover the needle after injection, into a recess, after which the needle shield is locked from movement.

As can be understood by the above mentioned examples, there are numerous combinations that are possible within the described invention. There is thus the possibility to have guided longitudinal movements, inclined movements, rotational movements, and combinations of these with the co-operating means according to the invention as well as locking of components either temporarily or fixed. There are also numerous possibilities of using and designing different surfaces of the co-acting components in order to obtain the desired function and interaction.

The principle according to the present invention may be used in a number of delivery devices such as injectors, mouth of nasal inhalers of powder or aerosol type, nebulizers, and the like where a number of functions are to be performed in order to deliver a dose.

One exemplary embodiment utilizing this principle is shown in the drawings 7-15. An injecting device comprises a generally tubular main body 110, an activation knob 112 and a needle shield 114, FIG. 7.

Figure 8:
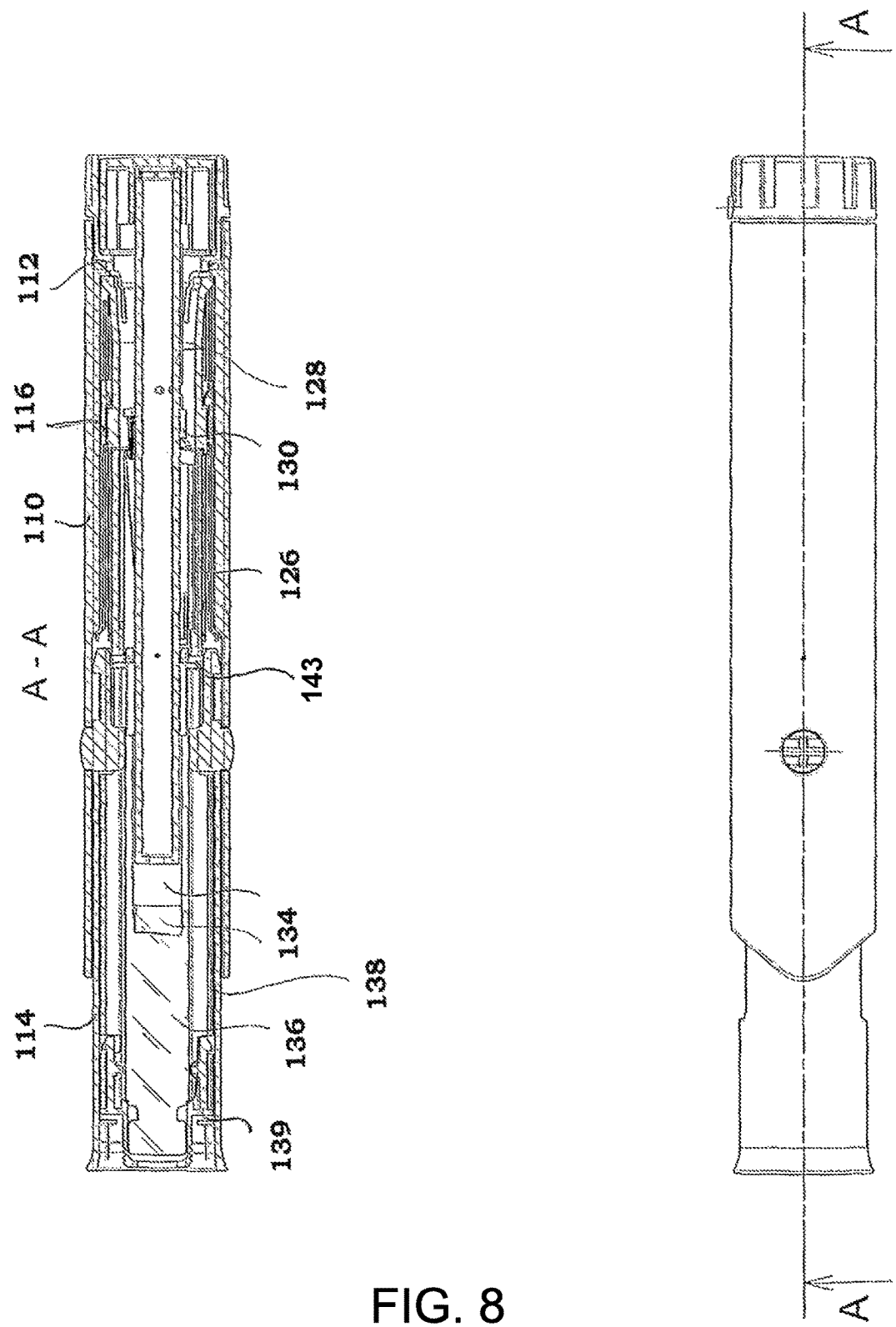
FIG. 8 is a cross-sectional view of the injector according to FIG. 7 taken at line A-A.
Figure 9:
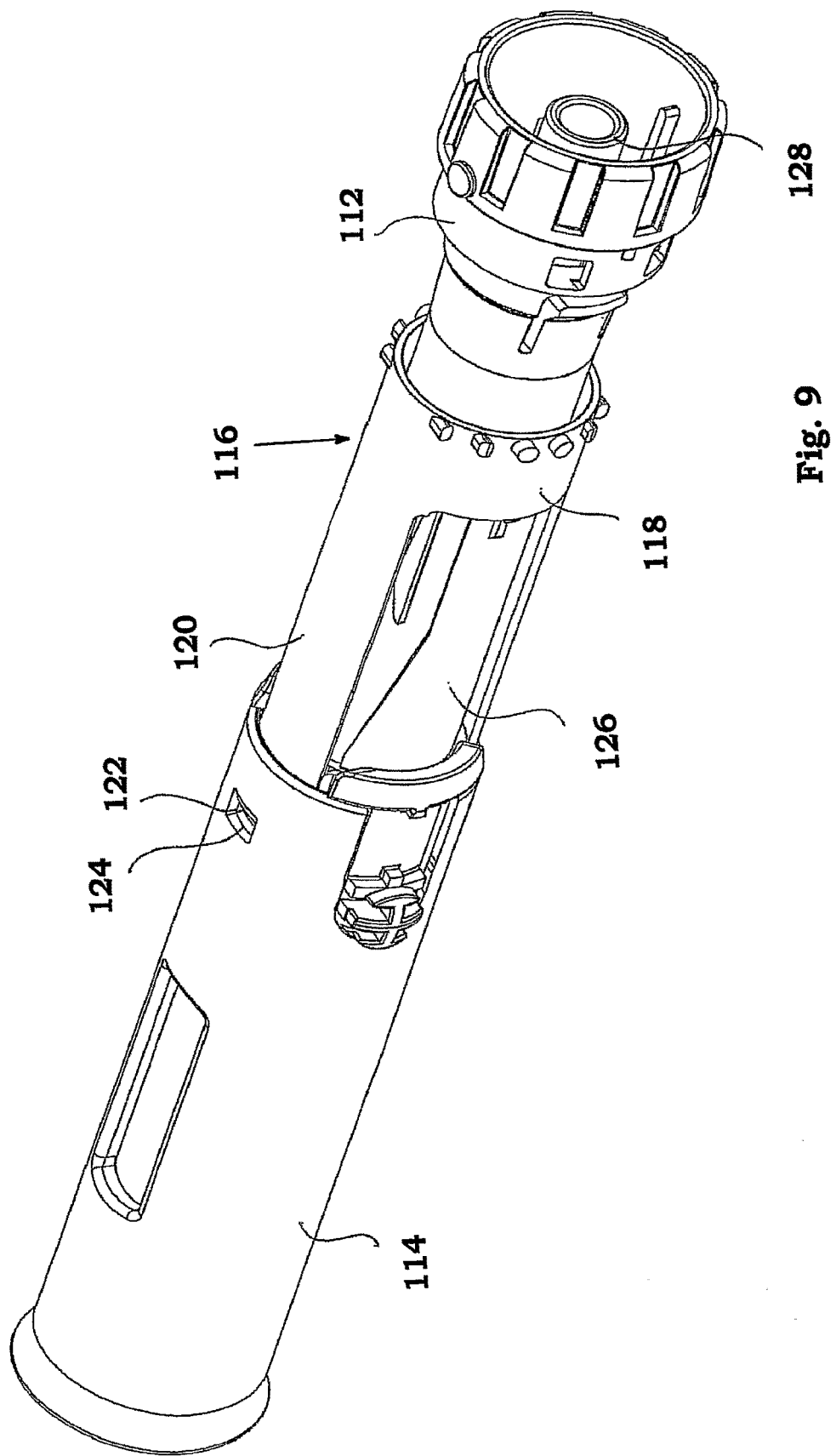
FIG. 9 is a perspective view of the injector according to FIG. 7 with the main tubular housing removed for simplicity.

The needle shield 114 is arranged slidably inside the main housing and is connected to a needle shield link 116, FIGS. 8 and 9. For clarity the main body is removed in FIG. 9. The needle shield link is arranged with an upper (to the right in FIG. 9) tubular part 118 and two longitudinally extending arms 120. The end of the arms are arranged with outwardly extending ledges 122, which fit into recesses or passages 124 in the upper part of the needle shield, thus obtaining the connection between the needle shield and the needle shield link.

Figure 13:
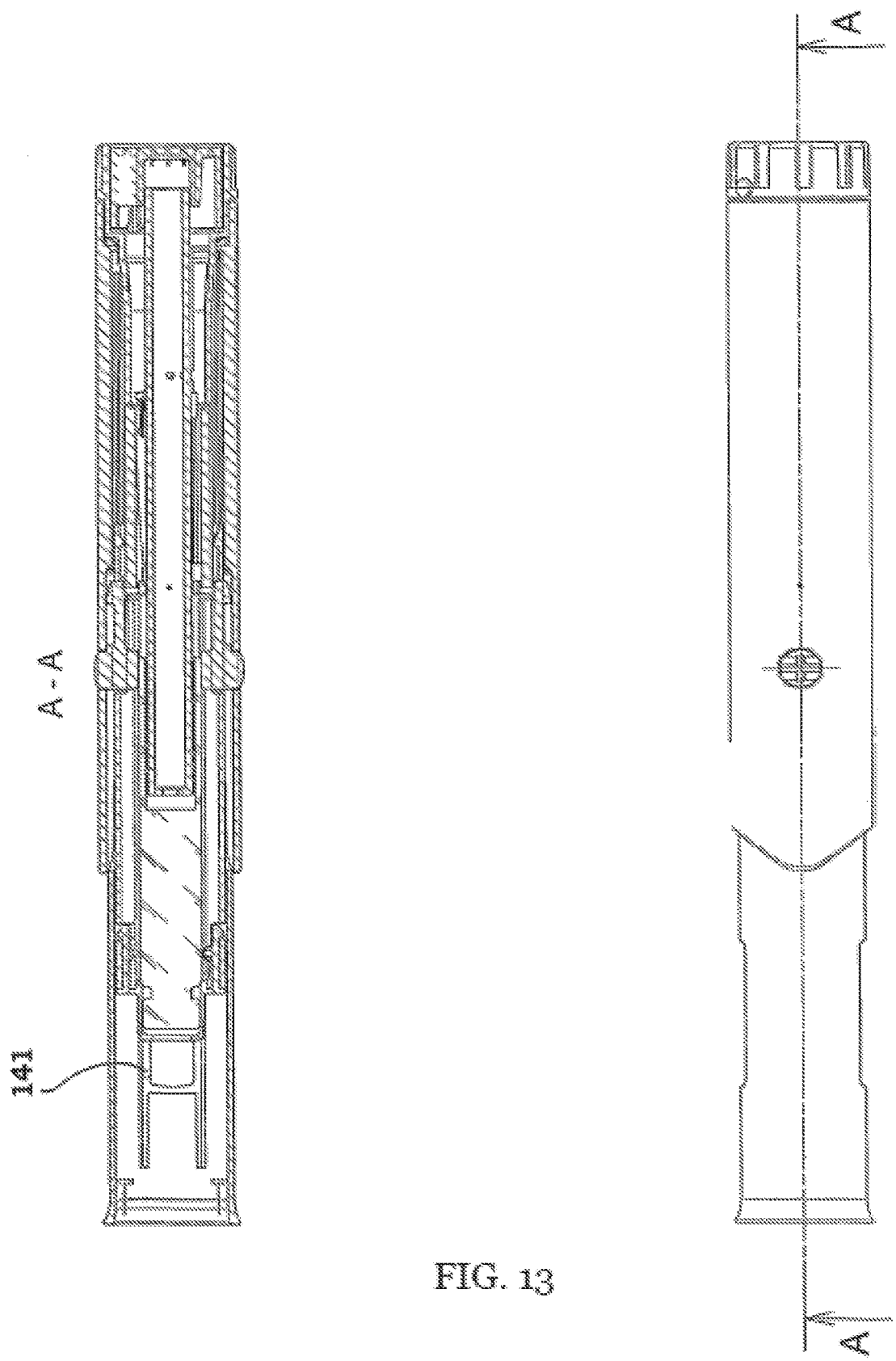
FIGS. 13-15 are cross-sectional views according to FIG. 8 during operation of the device.

Inside the needle shield link a generally tubular member 126, hereafter named rotator, is rotationally and slidably arranged. It is arranged with a number of ridges and protrusions on its outer surface which are to cooperate with guide members arranged on the inner surface of the needle shield link, the function of which will be explained below. The upper end surface of the rotator is in contact with the lower end surface of the activation knob 112, preventing longitudinal movement but allowing rotational movement between them. Inside the rotator, a plunger 128 is slidably arranged and movable with the help of an injection spring. The upper part of the plunger is arranged with a number of outwardly extending stop members 130, arranged to cooperate with inwardly extending stop members 132 on the inner surface of the activation knob, as will be explained below. The front end of the plunger is in contact with a stopper 134 arranged inside a cartridge 136 containing the medicament to be delivered to a patient. The cartridge is housed in a holder 138. The cartridge is held in the holder by an end piece 139 snap-fitted with holder. The lower end surface of the rotator is in contact with an end wall 143 of the holder. The holder is guided by the needle shield via grooves 141, FIG. 13.

A needle shield spring (not shown) is arranged to press on the needle shield link between a ledge on the housing and a ledge on the upper part of the needle shield link.

The device is intended to function as follows. When the device is assembled and delivered to the user the needle shield is in a retracted position inside the main housing, FIG. 8, and held in this position against the force of the needle shield spring by an outwardly extending knob 140 on the activation knob 112 abutting an inwardly extending knob 142 on the inner surface of the needle shield link 116, 11.

Figure 10:
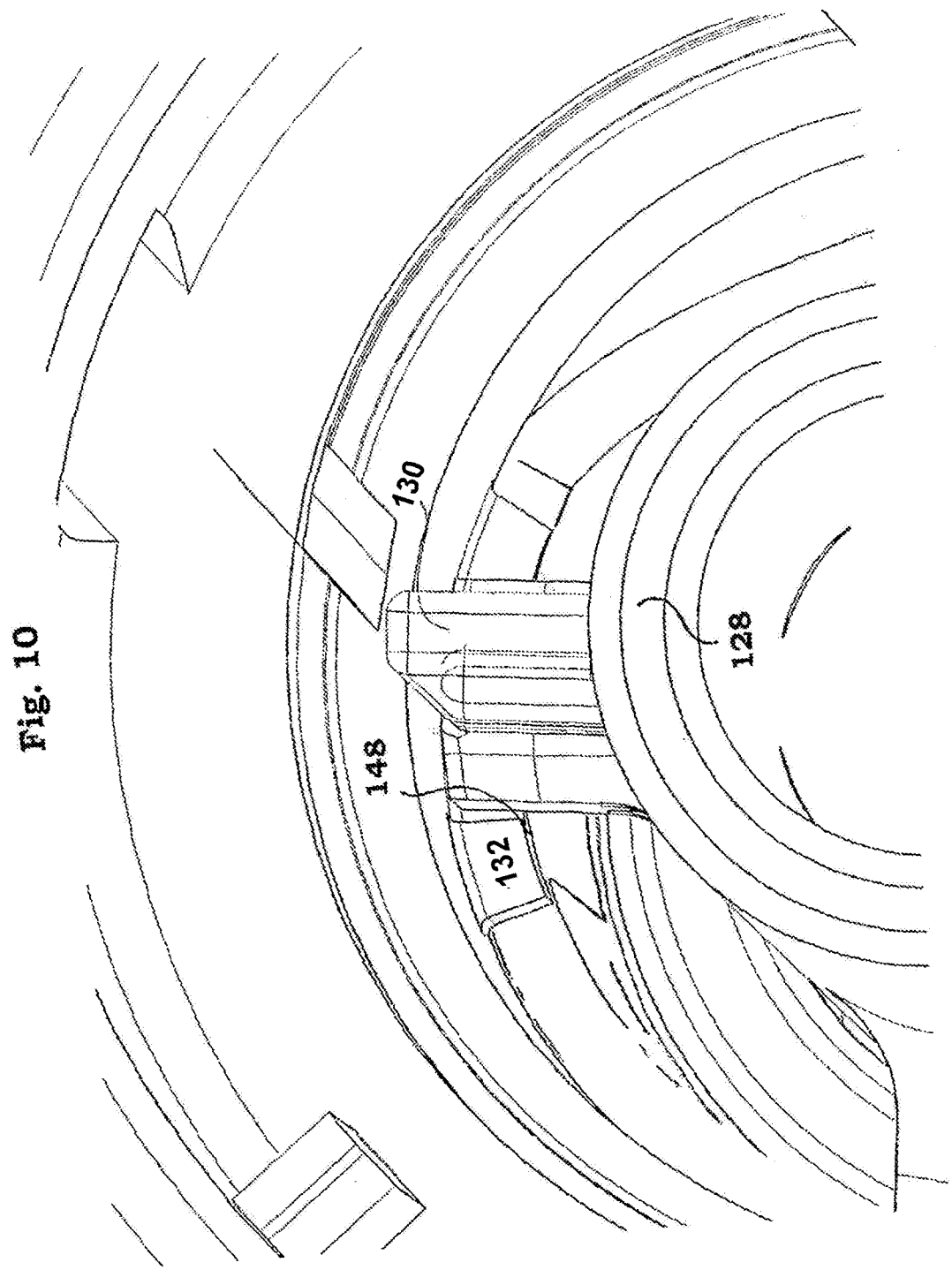
FIG. 10 is a detailed view of a part of the injector of FIG. 9.
Figure 11:
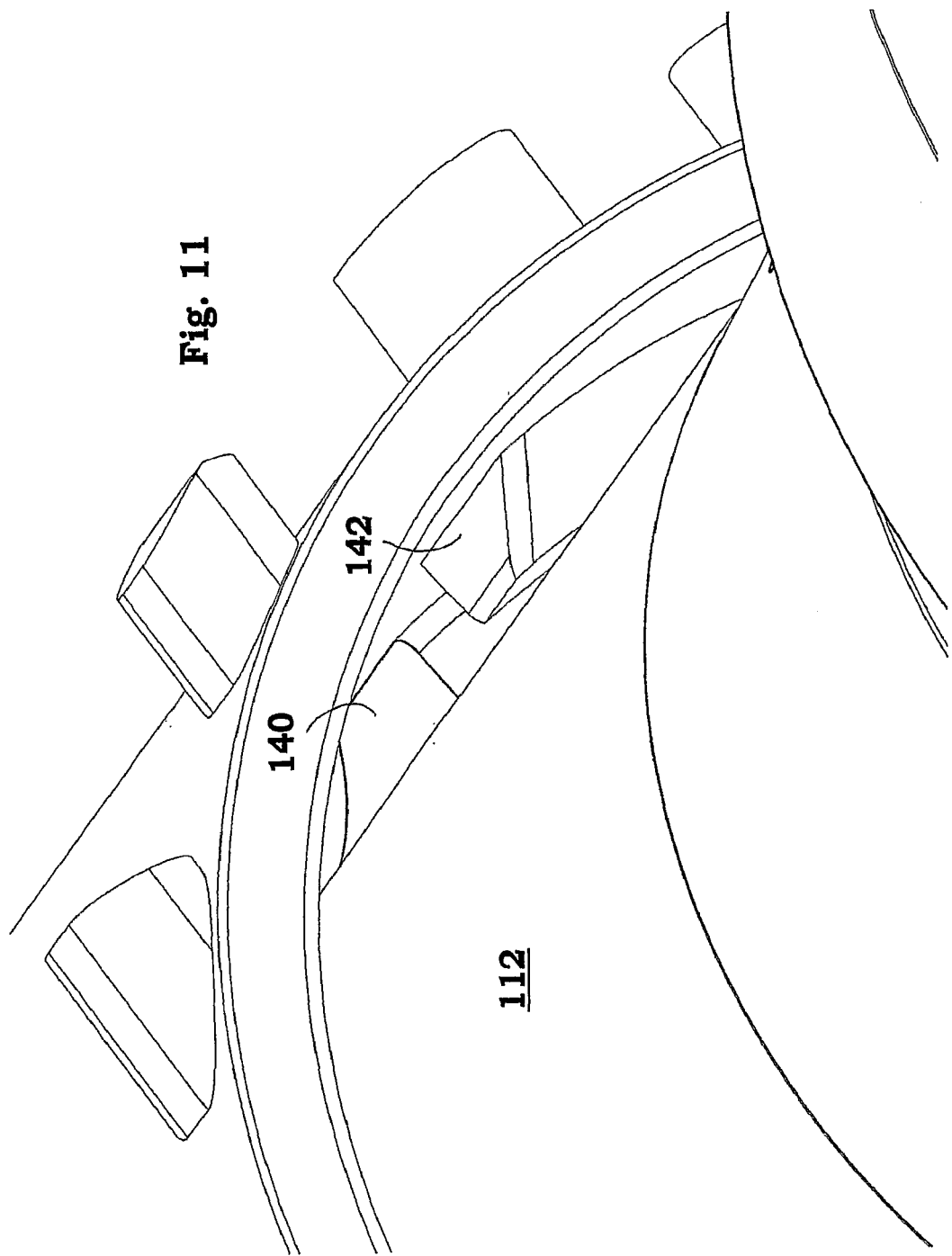
FIG. 11 is a detailed view of a dose activating means displaying first stop means.

The plunger 128 is in its rearmost position and the injection spring is tensioned. The plunger is held in this position by a set of oppositely arranged outwardly extending knobs 130, FIG. 10, on the plunger 128 abutting a first set of ledges 132 arranged on the inner surface of the activation knob 112. The ledges 132 are arranged with longitudinally extending protrusions 148 for admitting movement between the knobs 130 and the ledges 132 in only one direction.

When the patient is to use the device a new needle is attached to the lower, front, part of the cartridge by conventional means, such as screw threads or the like. Because the needle shield is in the retracted position, the cartridge end is easily accessible during attachment of the needle.

Figure 14:
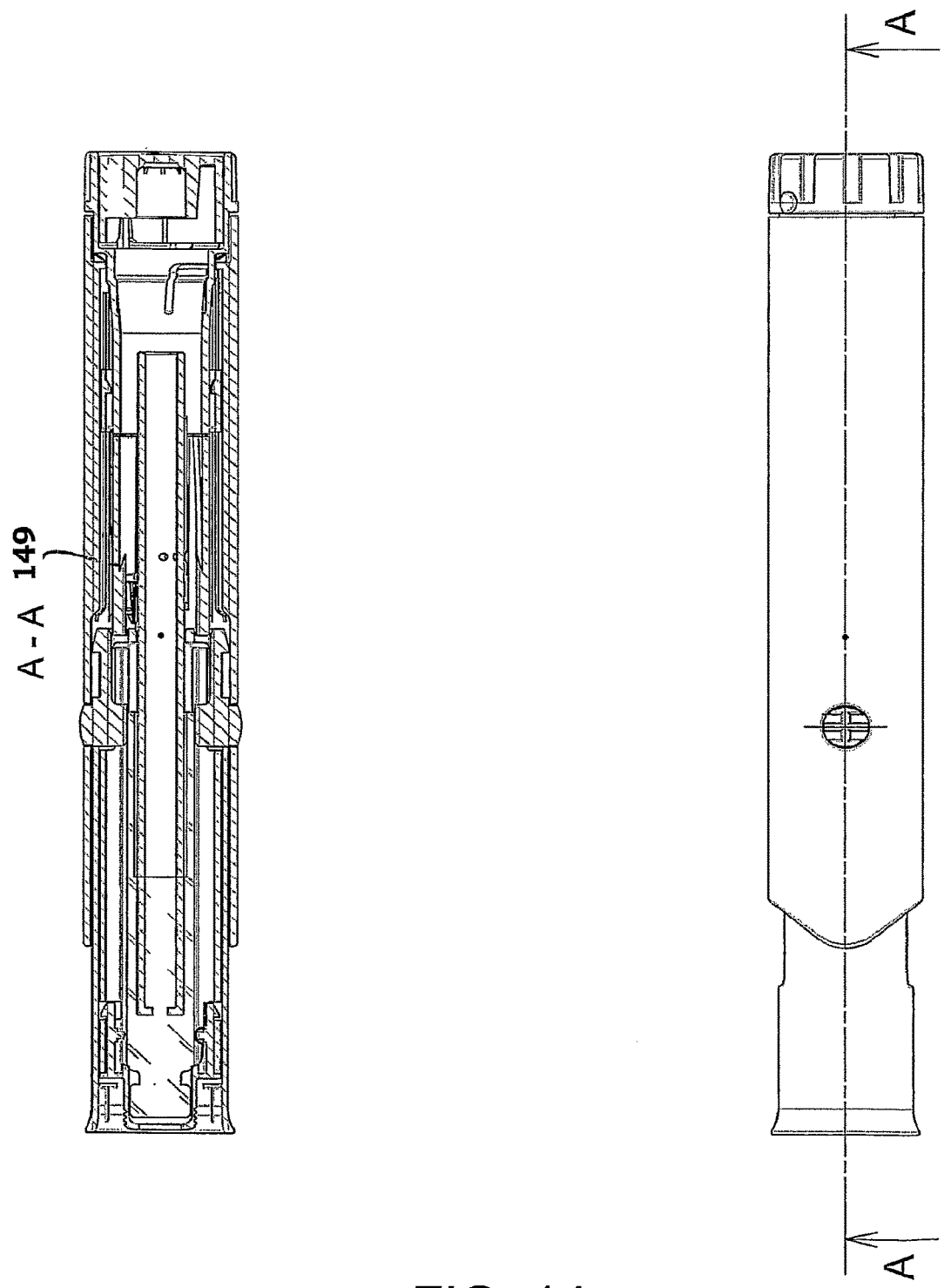

Thereafter the device is to be primed. The activation knob is then turned from the locked position to a start position, FIG. 13, which may be indicated on the main housing adjacent the activation knob. The turning of the knob causes the outwardly extending knobs 130 of the plunger 128 to slide off the ledges 132 of the activation knob, whereby the force of the injection spring pushes the plunger towards the cartridge and thus moves the stopper inside the cartridge, thereby pressing any prevailing air and some liquid out of the cartridge through the needle. The movement is stopped when the outwardly extending knobs 130 of the plunger abut a second set of ledges, 149, FIG. 14, arranged on the inner surface of the upper part of the rotator.

Figure 12:
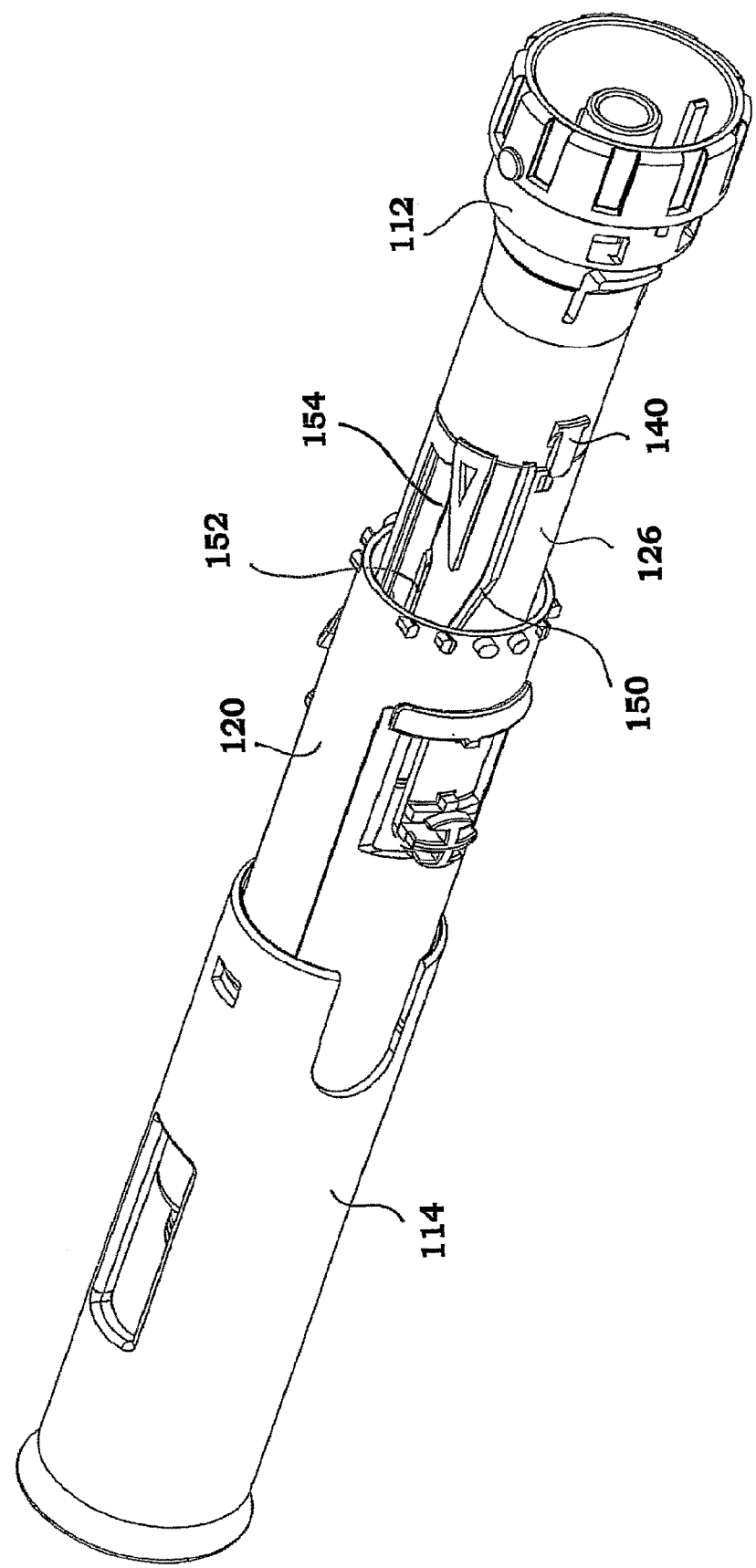
FIG. 12 is a view corresponding to FIG. 9 during operation of the device.

The turning of the activation knob also causes the outwardly extending knob 140 of the activation knob to be moved out of contact with the inwardly extending knob 142 of the needle shield link 116. The force of the needle shield spring then urges the needle shield and the needle shield link to an extended position, thereby covering the needle from sight, FIG. 13. The inner surface of the shield link is arranged with guide knobs, which during the movement to an extended position run along a guide surface 150, FIG. 12, having an inclination in relation to the longitudinal direction of the device. This causes the rotator to turn somewhat in relation to the needle shield link.

The device is now ready for injection. The needle shield is pressed against the injection site and the needle penetrates the skin. During the inward movement of the needle shield the guide knobs of the needle shield link run along longitudinally extending ridges 152, FIG. 12 until they come in contact with inclined ledges 154. The contact between these causes the rotator to turn during further movement of the needle shield and the needle shield link. The rotator is thus turned until the outwardly extending knobs 130 of the plunger slip off the second set of ledges arranged on the upper part of the rotator, thereby starting the injection. The plunger moves downward due to the force of the injection spring and the knobs 130 run in longitudinal grooves on the inner surface of the rotator. The movement of the plunger moves the stopper, whereby medicament is expelled through the needle, until the outwardly extending knobs 130 of the plunger abut the wall 143, FIG. 14.

Figure 15:
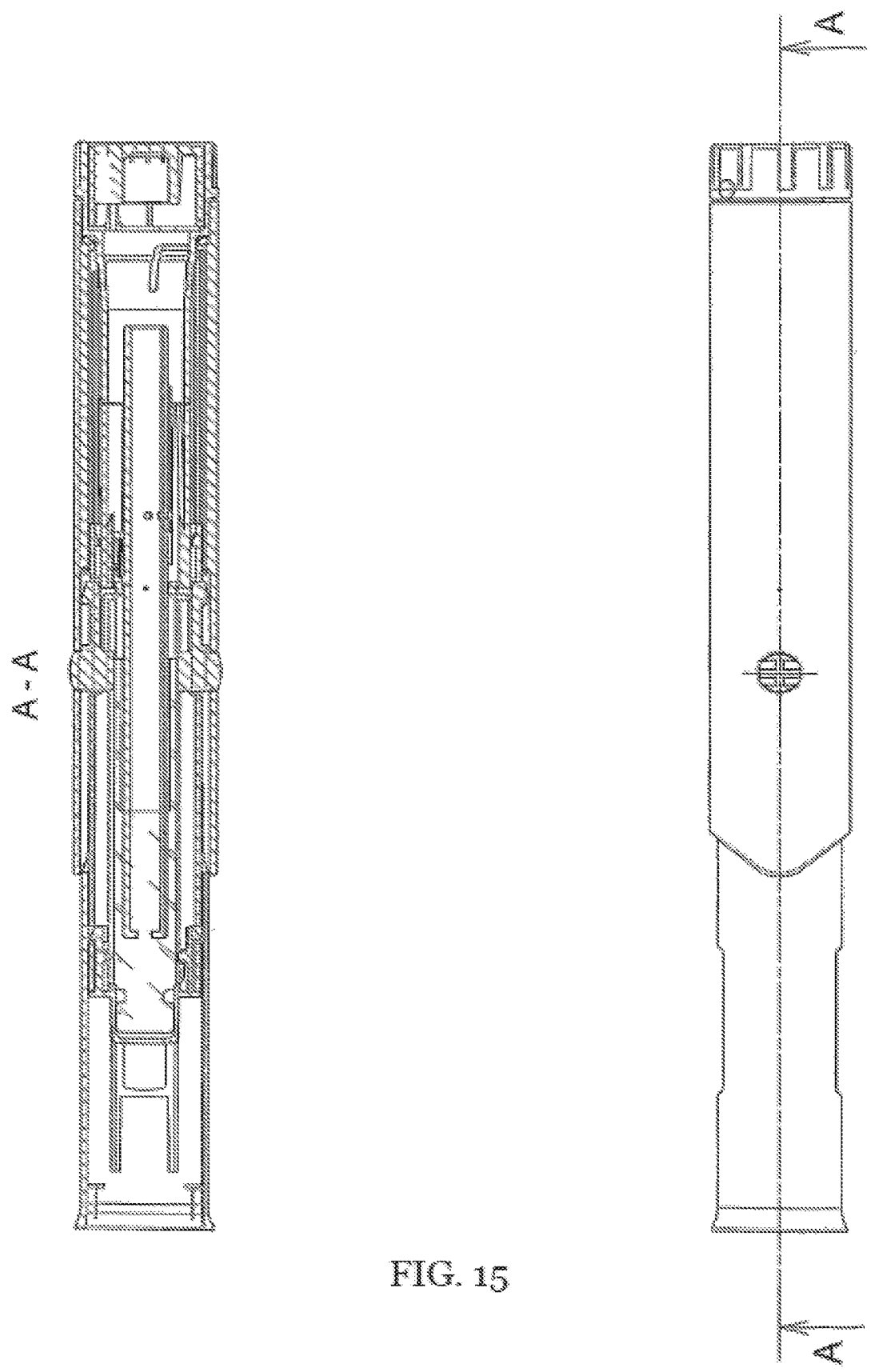
Figure 16:
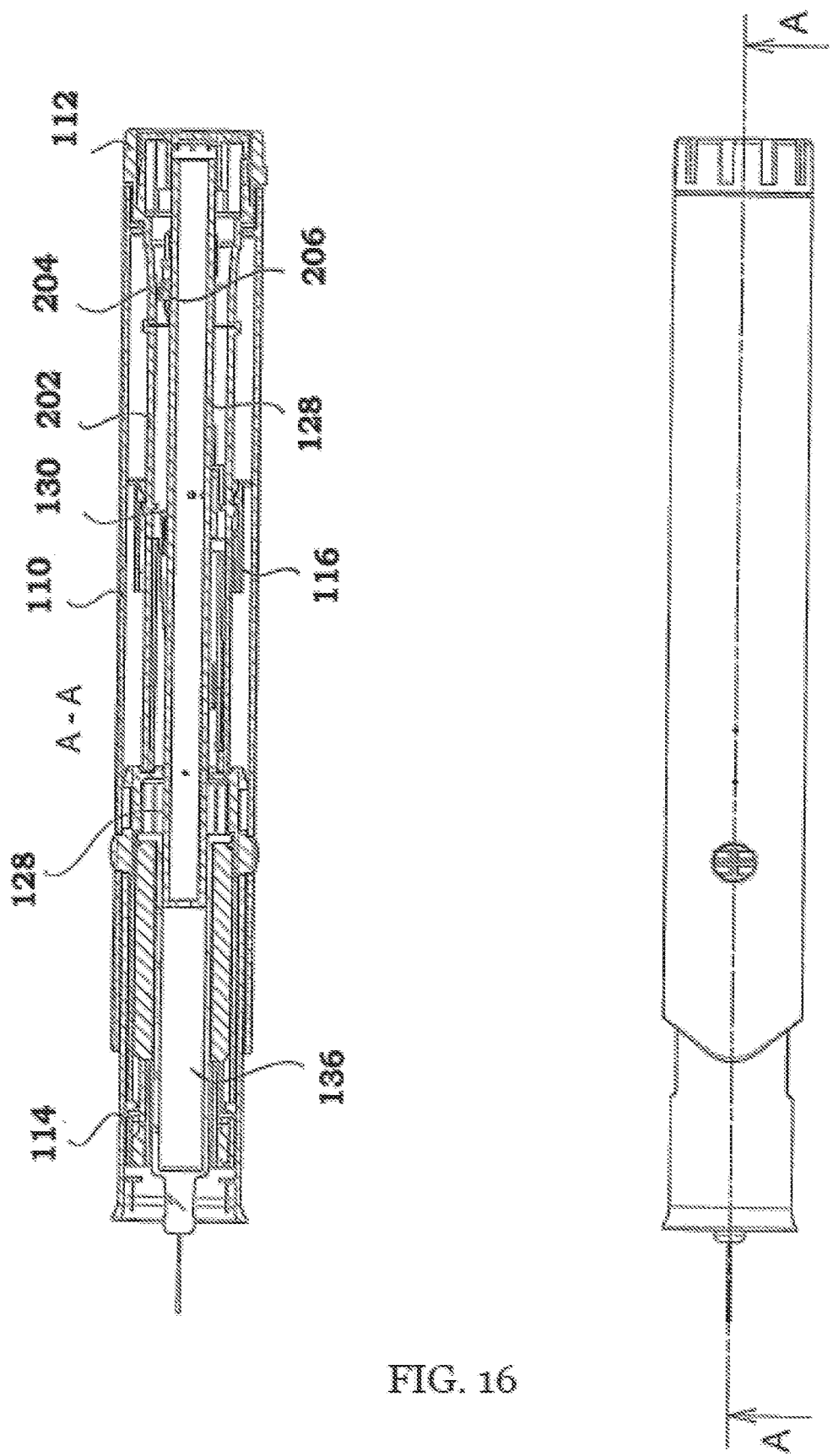
FIGS. 16-26 are cross-sectional views of a further embodiment of the present invention in different modes of operation.
Figure 17:
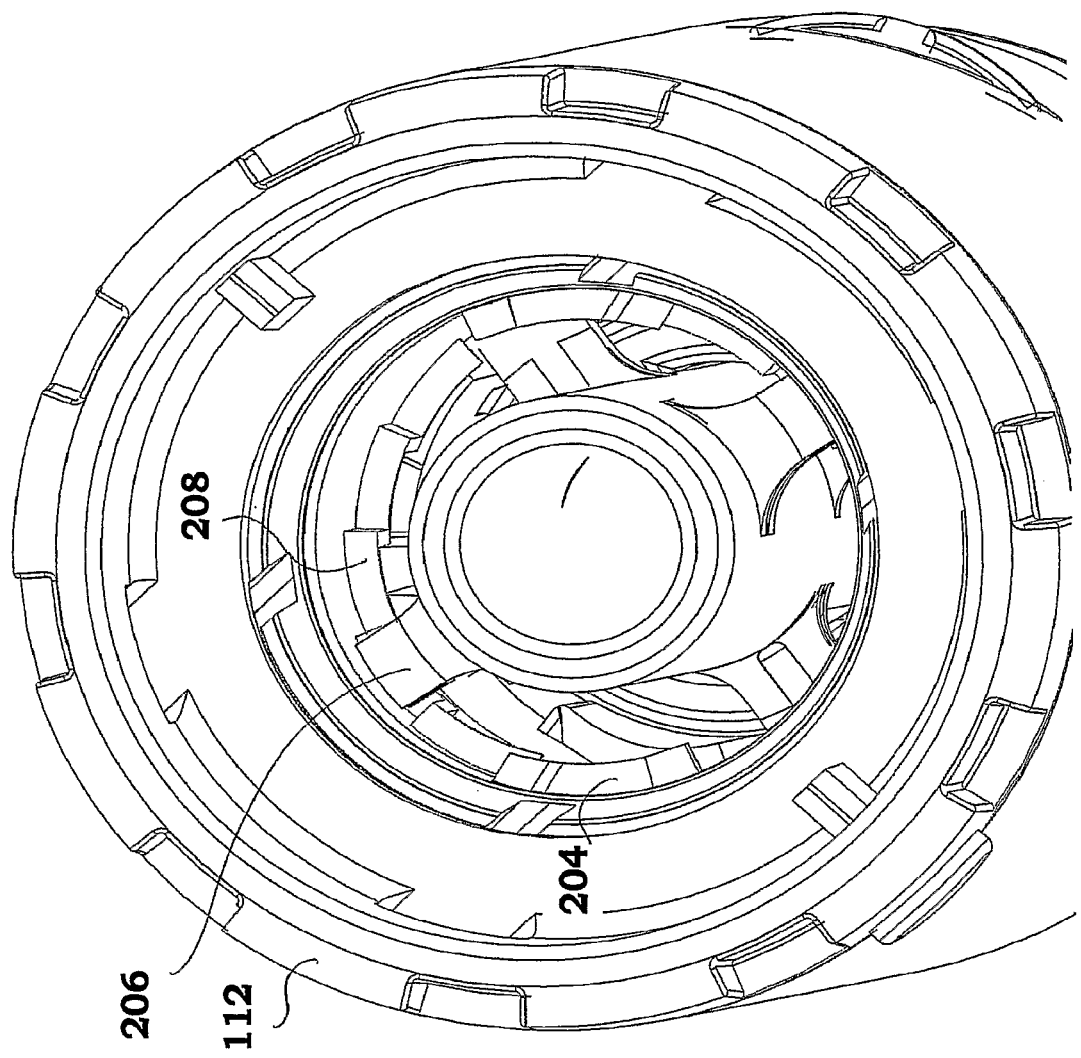
Figure 18:
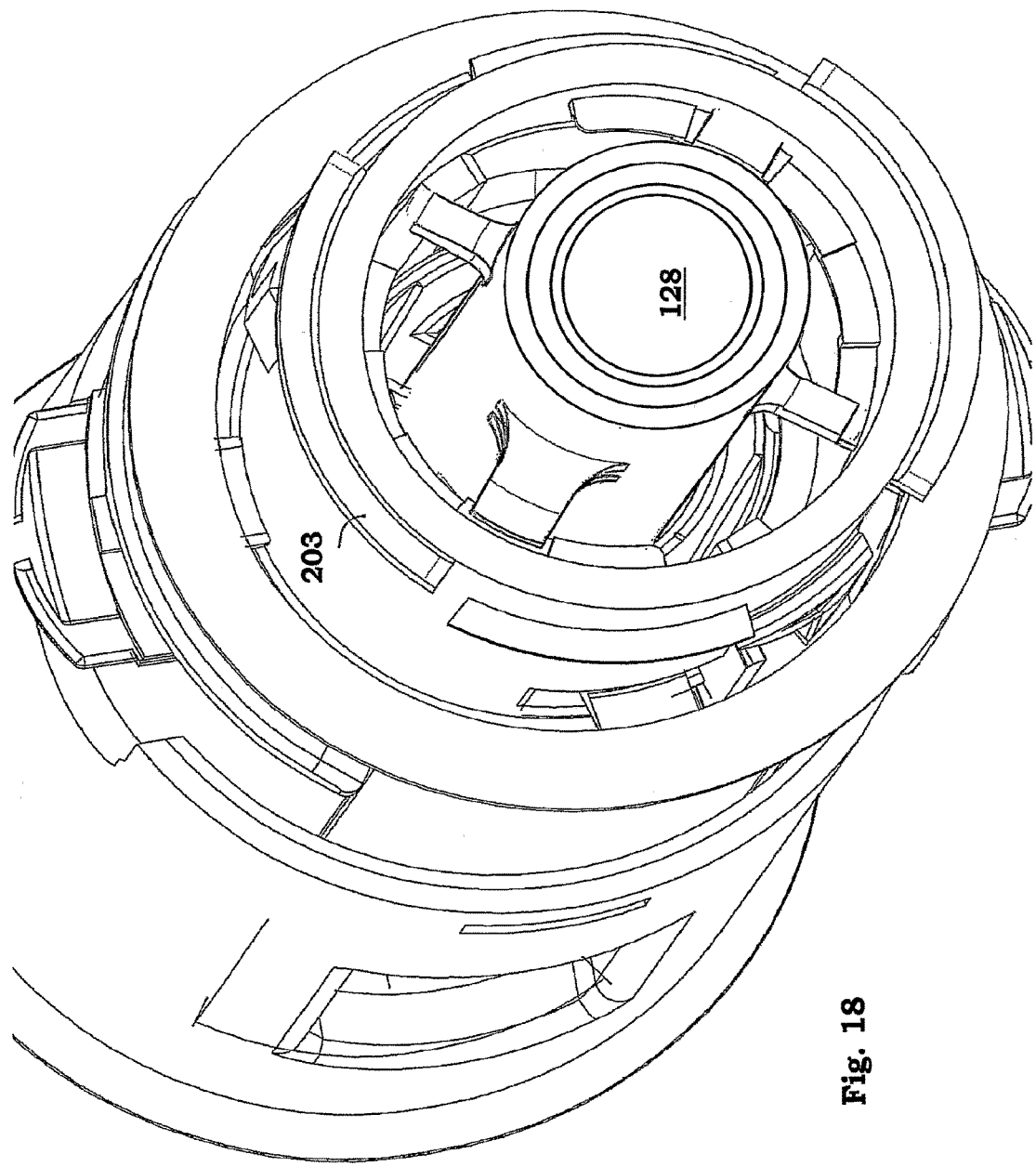
Figure 19:
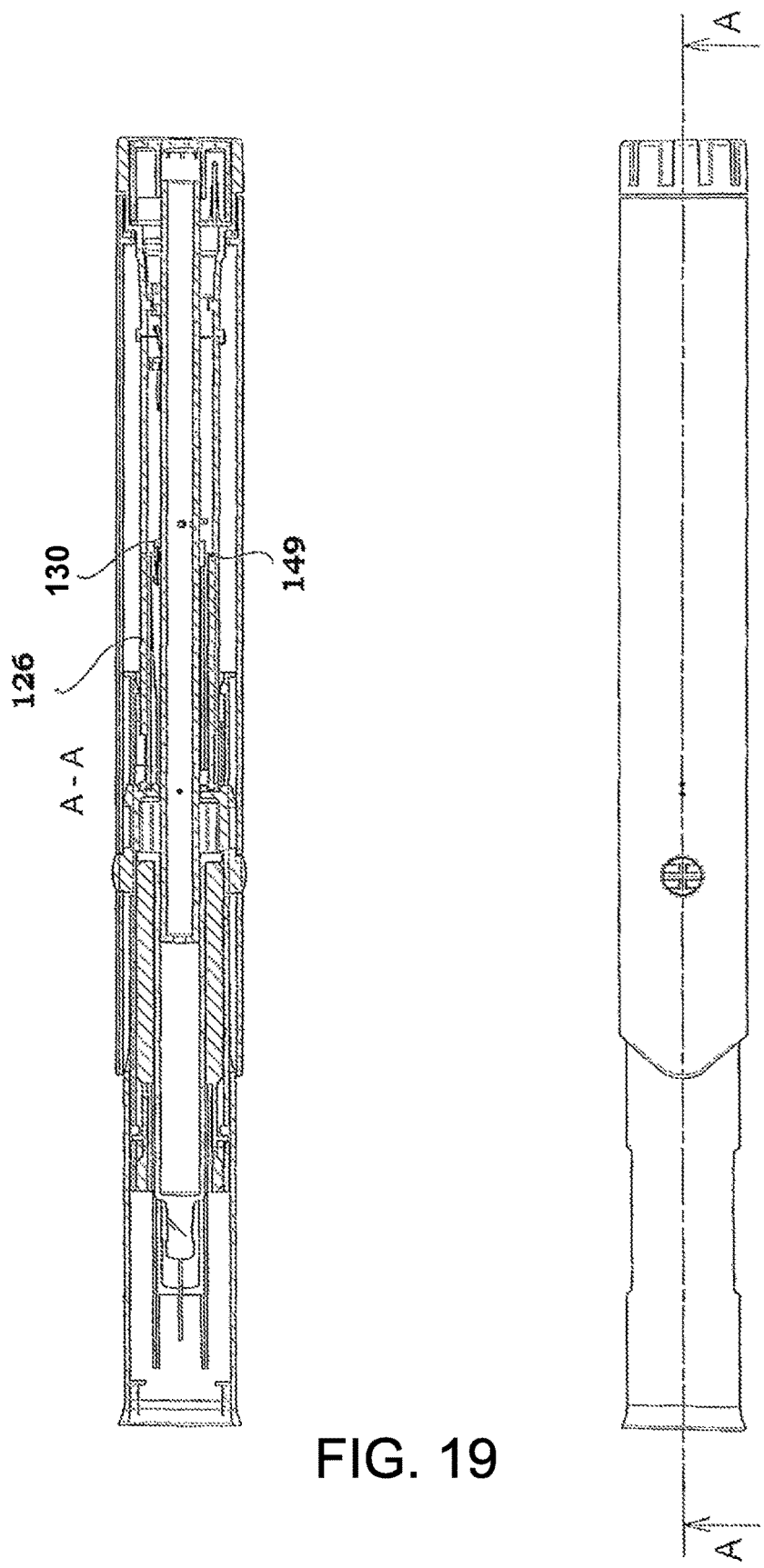

When the injection is finished, the user removes the device from the injection site, whereby the needle shield and the needle shield link moves into an extended position. The guide knobs of the needle shield link now move along the other side of the ridges 152 and at a certain position along this path, when the needle shield is in its most extended position covering the needle, the guide knobs fit into recesses in the rotator, thereby locking the needle shield in the extended position, preventing the needle shield to be pushed in again, FIG. 15. The risk of unintentional needle sticks is thus eliminated.

FIGS. 16 to 26 show a second embodiment of the present invention. The second embodiment comprises a further feature namely a dose setting means. This feature can be used to provide injectors for different medicaments and/or different doses depending on the type of disease and/or type of patient. With the feature, the same injector can be used to deliver different doses independent of the design of the injector. The first embodiment had a design that enabled a certain dose quantity, which was dependent on the actual design or stroke of the injector, which in turn means that if you would like to use the injector for a different dose quantity, the design, and thus the plastic moulding forms, had to be changed. The previous design is perfectly usable when the medicament always is to be delivered in a certain quantity.

As mentioned a main difference with the second embodiment is the dose setting function. It comprises a second generally tubular member 202 arranged between the dose setting knob 112 and the rotator 126, FIG. 16. The tubular member 202 is rotationally locked to the dose setting knob by outwardly extending, oppositely arranged claws 203, FIG. 18, between which corresponding inwardly extending claws on the dose setting knob fit. As with the first embodiment, the plunger is held in an initial position by a set of oppositely arranged outwardly extending knobs 206, FIG. 21 on the plunger 128 abutting a first series of ledges 204 arranged on the inner surface of the dose setting knob 112. The ledges are designed in the same manner as for the first embodiment. The turning of the knob, FIG. 23, after attaching a needle at the front end of the injector, to a start position for priming, causes the knobs to slide off the ledges. The force of the plunger spring pushes the plunger forward, expelling any prevailing air in the cartridge. The movement is stopped when the outwardly extending knobs 130 of the plunger abut a second set of ledges 149 as for the first embodiment, arranged on the inner surface of the rotator 126.

Figure 20:
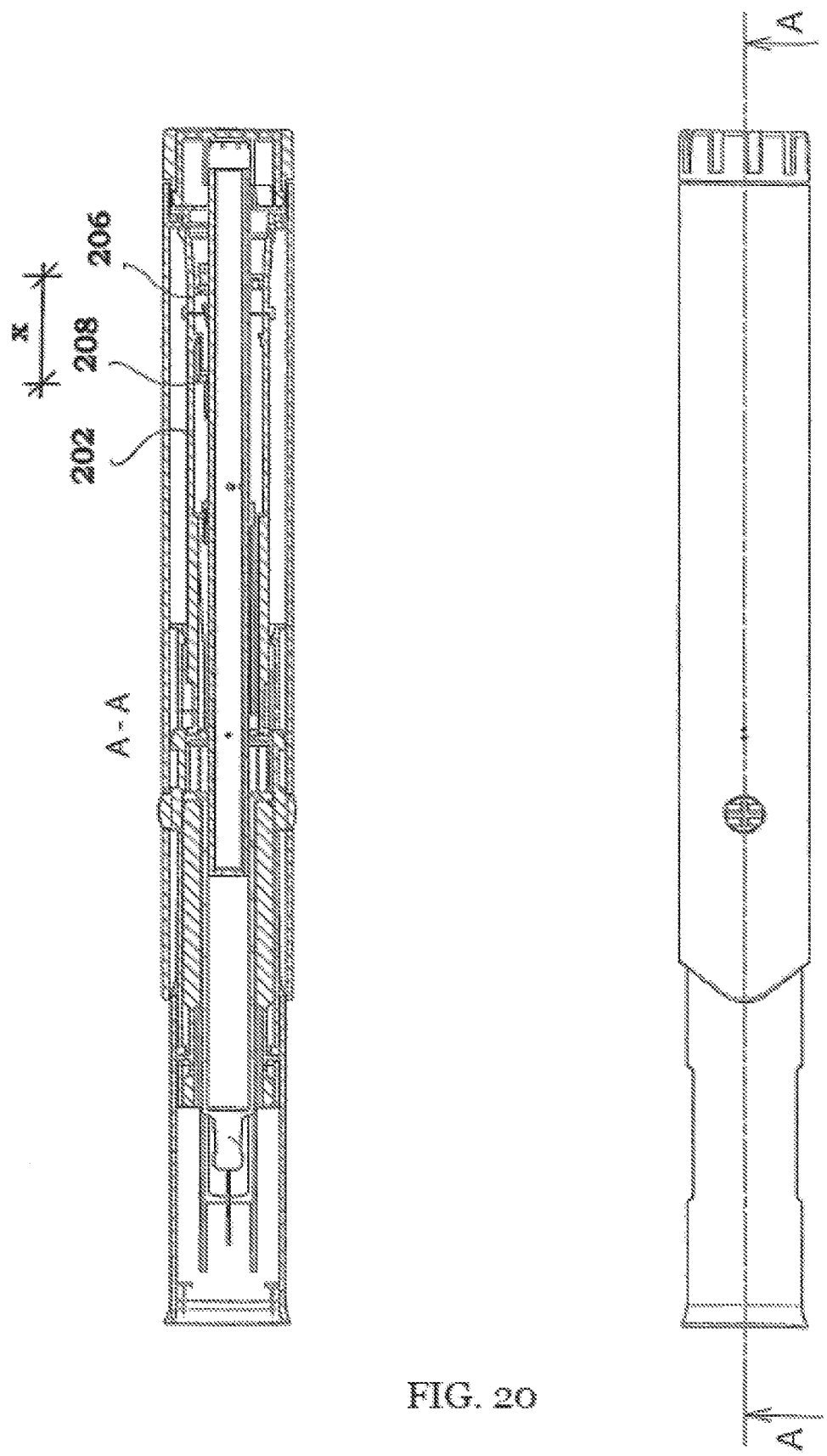
Figure 21:
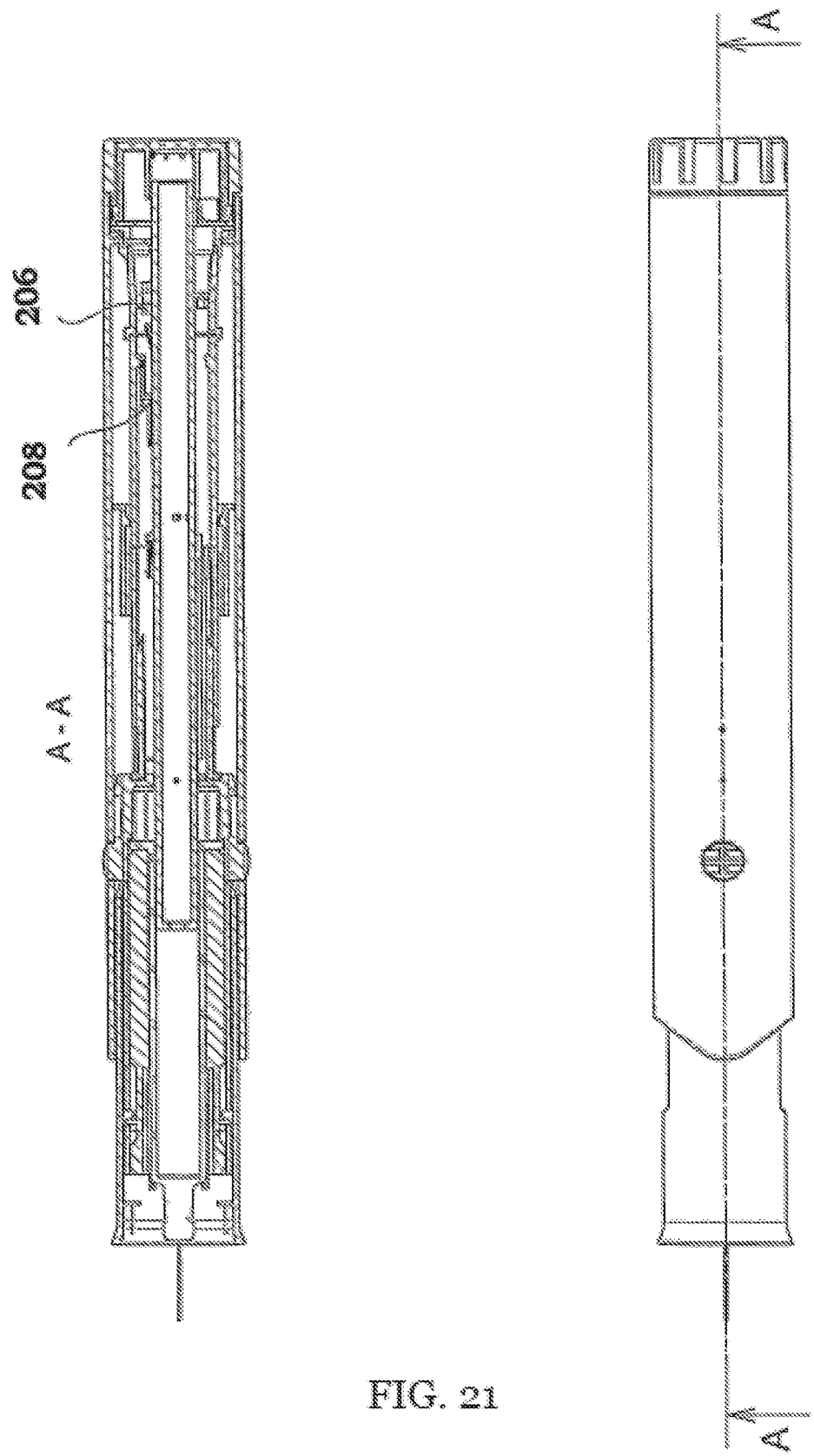
Figure 22:
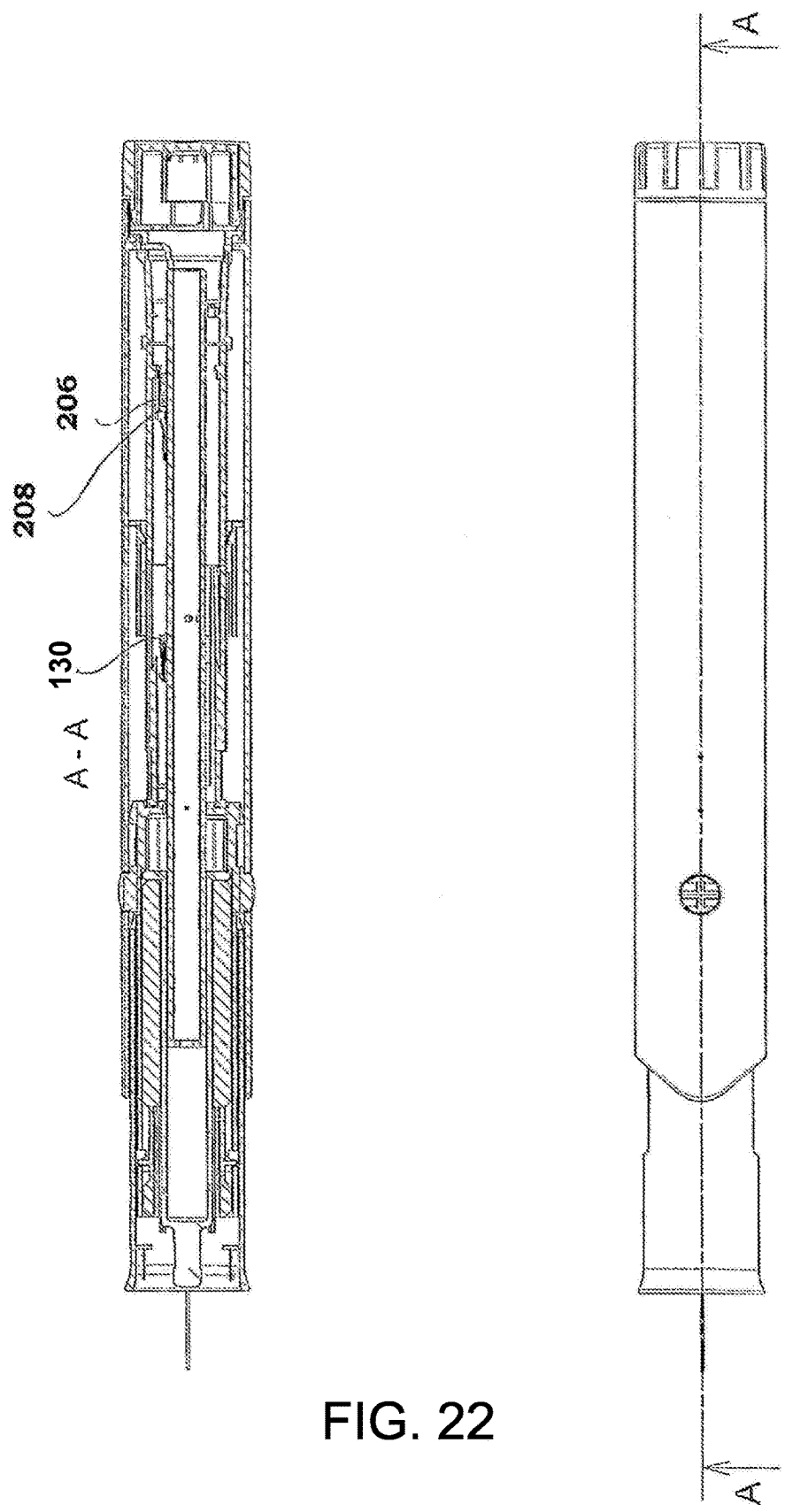

The dose setting knob is now free to be turned to set a certain dose, FIG. 20. For this purpose the inner surface of the tubular member 202 is arranged with a series of ledges 208, FIG. 17, at certain distances from the upper end of the injector, forming a set of descending ledges. Each ledge corresponds to a certain dose to be delivered. The turning of the knob is indicated by appropriate symbols or signs to tell the user which dose is set. As shown in FIG. 20, the distance x corresponds to the length of the plunger to travel during injection, and thus corresponding to the delivered dose.

The device is now ready for injection. When pressing the device against the injection site and penetrating the skin, FIGS. 21 and 22, the guide knobs of the needle shield link rotate the rotator as for the first embodiment, whereby the outwardly extending knobs of the plunger slip off the second set of ledges 149. This causes the plunger to move forward causing an injection until the outwardly extending knobs 206 abut one of the descending ledges 208 that is set for a certain dose, FIG. 22.

Figure 23:
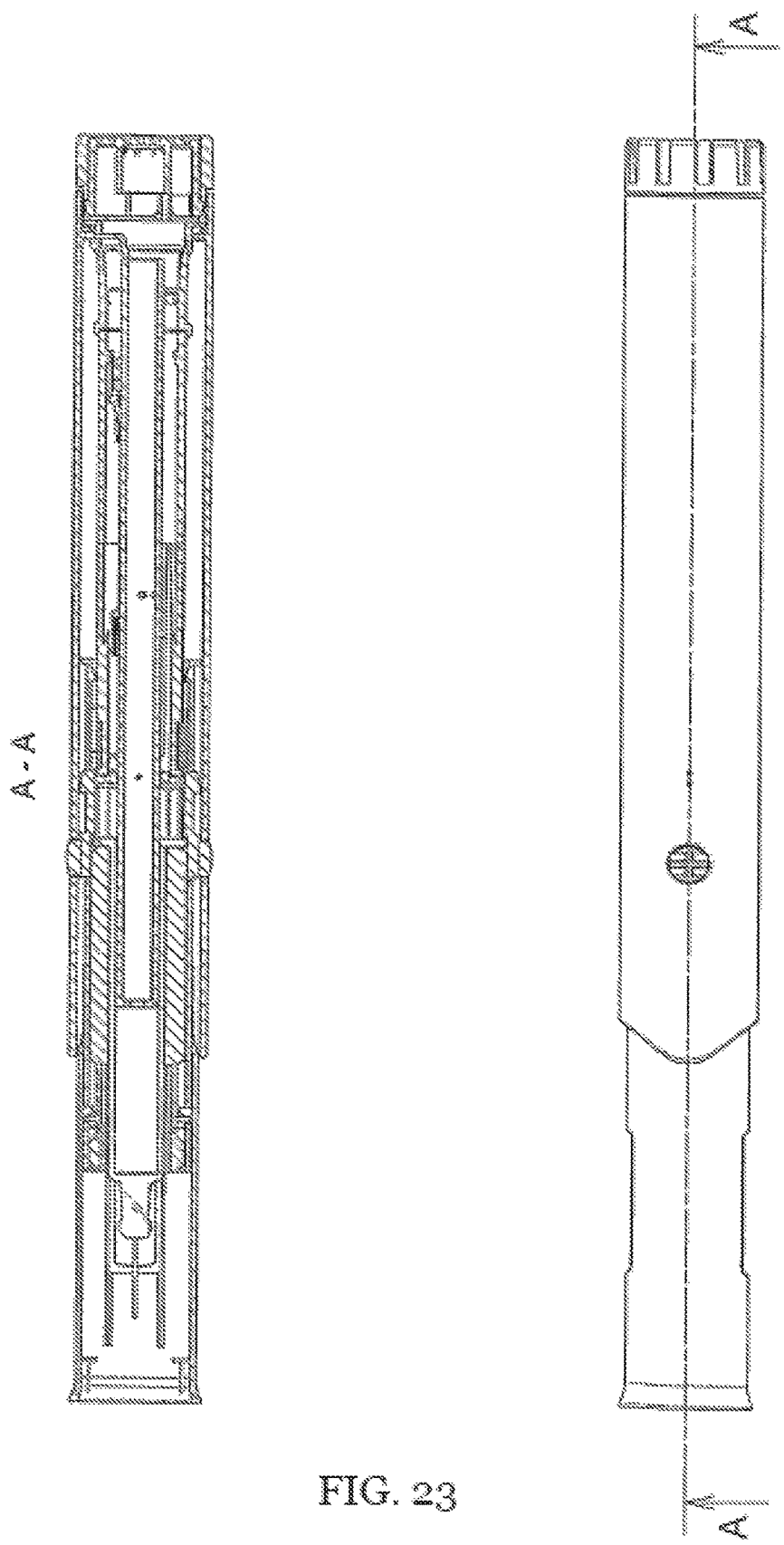
Figure 24:
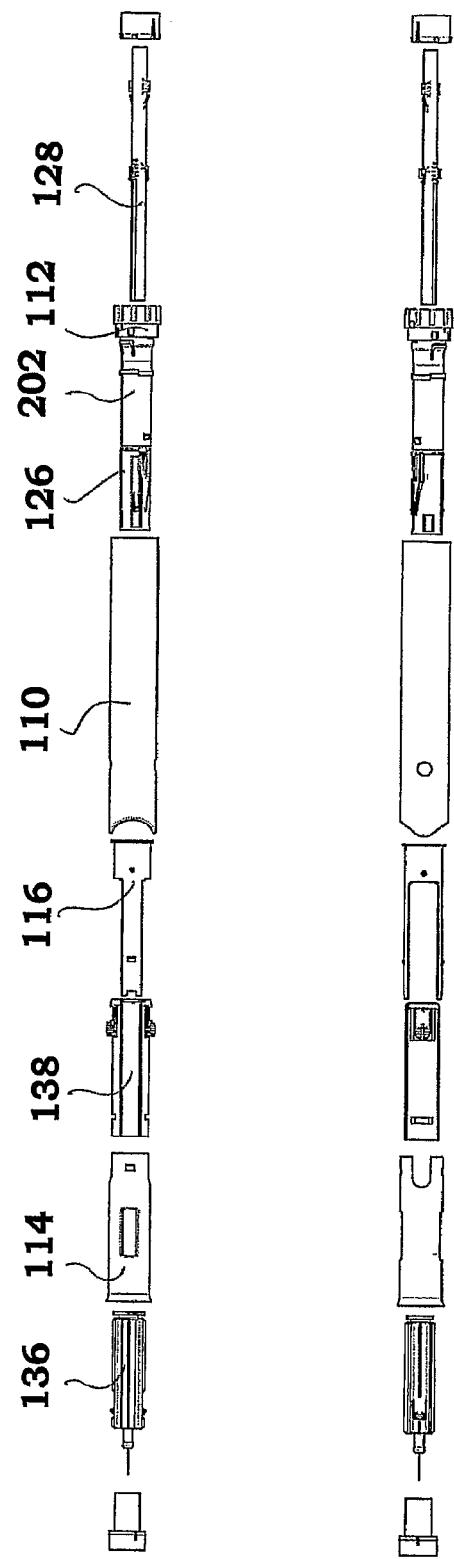

When the injection is finished the user removes the device and the same operation is performed by the device as for the first embodiment, FIG. 23.

Figure 25:
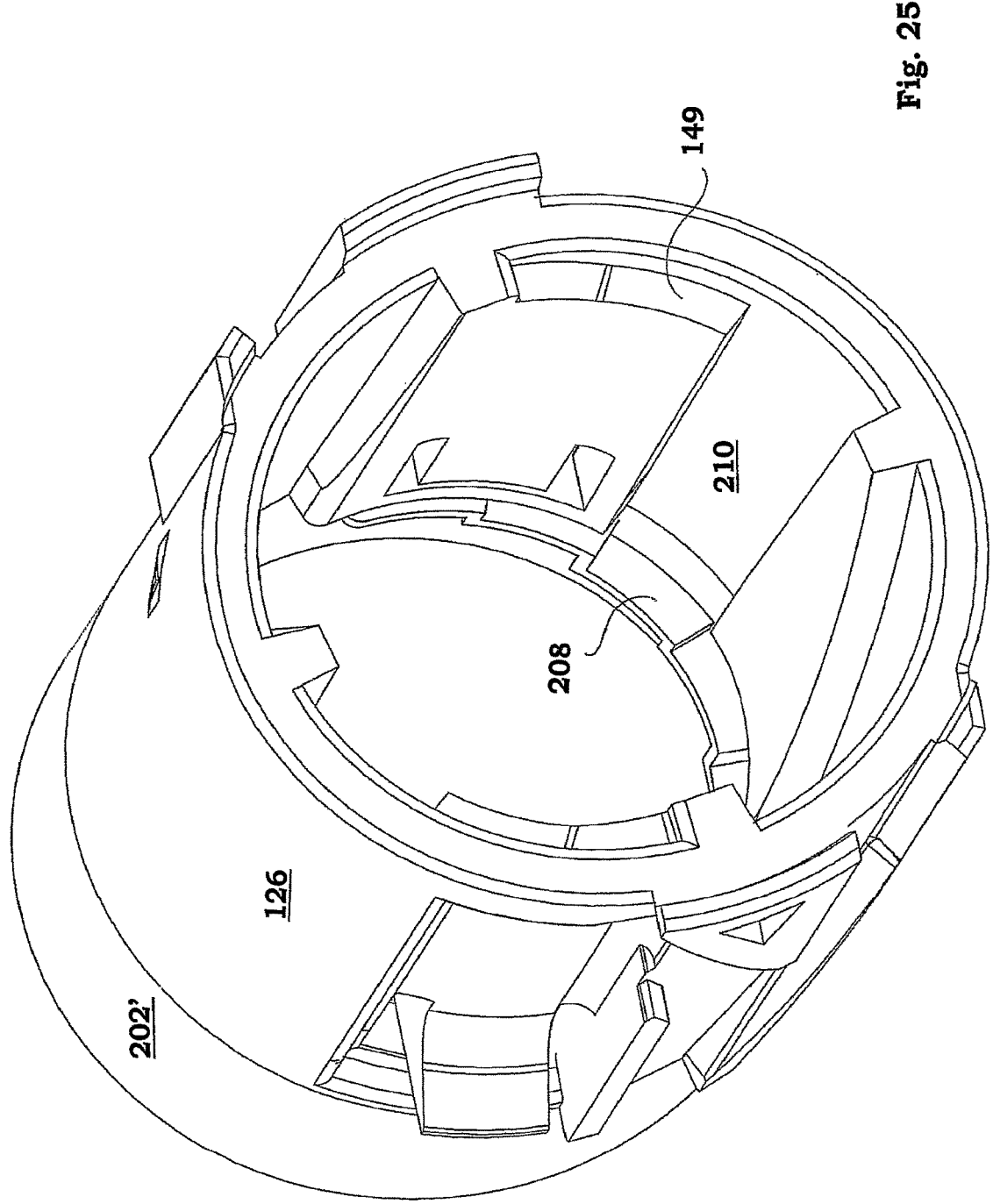
Figure 26:
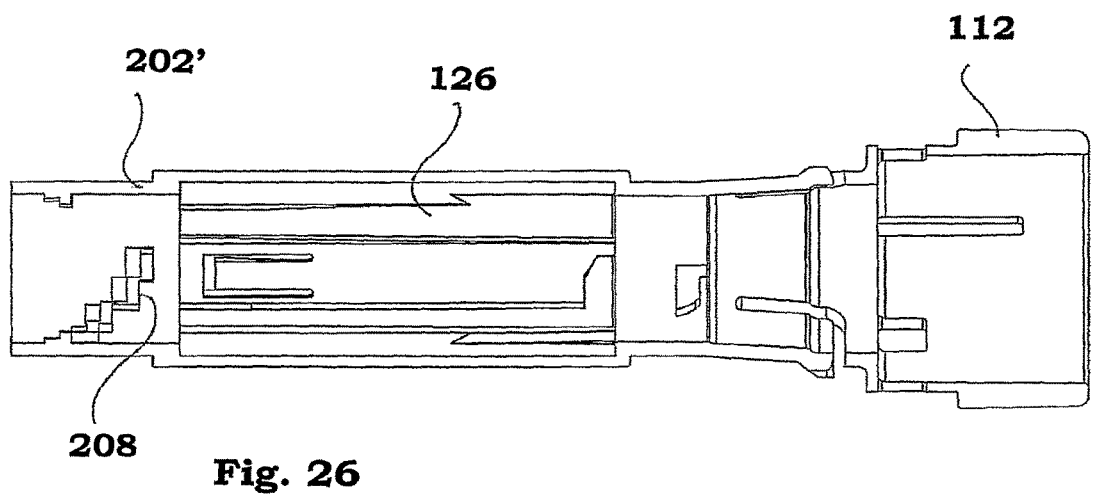

FIGS. 25 and 26 show a variant 202' of the tubular member 202 in connection with the rotator 126. This variant is intended to be placed between the rotator 126 and the end wall 143 of the holder, rather than between the dose setting knob and the rotator. The rotator is arranged with a second stop ledge 149 onto which the knob 130 of the plunger rest after priming. When the rotator is turned due to that the needle shield is pushed in during penetration, as is described above, the knob is pushed off the ledge 149 and runs down a groove 210 due to the force of the injection spring and thereby the forward movement of the plunger, causing an injection. The injection is stopped when the knob hits one of the dose ledges 208 of the tubular member 202'. FIG. 26 show how the tubular member 202' is attached to the dose setting knob with this arrangement having the rotator between them.

It is above described that the movement of the plunger from the locked delivery position to the position defined by the first stop ledge is the end of priming, i.e. deareating the syringe 136. It may also be that, for dual chamber cartridges, this movement includes a mixing step, i.e. the plunger moves a stopper inside the cartridge to a position where two substances contained in the cartridge, and initially held separated from each other by the stopper, are mixed. A subsequent attachment of a needle causes a priming of the mixed cartridge, due to the pressure from the plunger on the mixed solution, whereby the plunger can move forward to the stop ledge and be ready for an injection. In this case the travel of the plunger for mixing usually has to be longer than for a mere priming, but this design difference is easily feasible within the injector concept.

In the embodiments shown, the needle shield has been held in a retracted position inside the housing until activated. It is of course conceivable that the needle shield is in an extended position from the beginning and is only in a retracted position inside the housing during the penetration and injection steps. Further, even though a cartridge is described in the description of embodiments, other types of medicament containing enclosures may be used, such as ampoules, containers, etc.

It is to be understood that the above described and shown embodiment of the present invention is to be regarded as a non-limiting example and that it can be modified within the scope of the patent claims.

The invention claimed is:

1. A medicament injection device comprising:
   a needle shield;
   a plunger; and
   a tubular rotator, wherein:
   said tubular rotator is configured to be rotationally and slidably arrangeable at least partially inside said needle shield of said medicament injection device, and said tubular rotator is configured to slidably and moveably receive said plunger of the medicament injection device inside, so as to enable a relative movement between said tubular rotator, said needle shield, and said plunger,
   said tubular rotator comprises a plurality of ridges and a plurality of protrusions on an outer surface of said tubular rotator,
   one or more of at least one of the plurality of ridges or at least one of the plurality of protrusions are configured to slide on guide members arranged on an inner surface of the needle shield, so as to cause relative rotation between the tubular rotator and the needle shield, and
   said relative rotation causes the plunger to move from a first position in which said tubular rotator restricts movement of the plunger to a second position in which the plunger is allowed to act on a content of said medicament injection device.

2. The medicament injection device according to claim 1, further comprising:
   a tubular elongated main body; and
   a needle shield spring surrounding the needle shield, said needle shield being slidably arranged in the tubular elongated main body.

3. The medicament injection device according to claim 2, further comprising a dose activating means.

4. The medicament injection device according to claim 3, wherein said needle shield is configured to be in a retracted position inside the main body and to be held in this position against the force of the needle shield spring by an outwardly extending knob on the outer surface of said dose activating means abutting an inwardly extending knob on the inner surface of the needle shield.

5. The medicament injection device according to claim 4, wherein said dose activating means is adapted, when turned, to cause a rotation of said tubular rotator, whereby said outwardly extending knob on said dose activating means is moved out of contact with said inwardly extending knob of said needle shield, and then the force of said needle shield spring urges said needle shield to an extended position and thereby covering the needle from sight.

6. The medicament injection device according to claim 5, wherein said plurality of ridges and said plurality of protrusions comprise longitudinally extending ridges and inclined ledges on the outer surface of the tubular rotator, and
   wherein said guide members of the needle shield is configured, during an inward movement of said needle shield, to run along the longitudinally extending ridges on the outer surface of the tubular rotator until said guide members come in contact with the inclined ledges on the outer surface of the tubular rotator.

7. The medicament injection device of claim 6, whereby said contact between said guide members and the inclined ledges causes the tubular rotator to turn until outwardly extending stop members of said plunger slip off a set of ledges arranged on an upper part of the tubular rotator, thereby moving said plunger downward due to the force of the injection spring and ejecting medicament through the needle.

8. The medicament injection device of claim 7, wherein said needle shield is adapted to move axially in relation to said tubular rotator to an extended position by a turning of said dose activating means.

9. The medicament injection device of claim 8, wherein said needle shield is further adapted to move axially in relation to said tubular rotator to a retracted position by the inward movement of said needle shield.

10. The medicament injection device of claim 9, wherein said needle shield is further adapted to move again axially in relation to said tubular rotator to the extended position by having the guide members of the needle shield move along the other side of said longitudinally extending ridges.

11. The medicament injection device according to claim 1, wherein said tubular rotator comprises a plurality of ledges arranged on the inner surface of an upper part of the tubular rotator and configured to cooperate with outwardly extending stop members on an outer surface of said plunger.

12. The medicament injection device according to claim 11, wherein said plurality of ridges and said plurality of protrusions comprise longitudinally extending ridges and inclined ledges on the outer surface of the tubular rotator arranged and configured such that the guide members of the needle shield are runnable along one side of said longitudinally extending ridges until said guide members come in contact with said inclined ledges.

13. The medicament injection device according to claim 12,
whereby said contact between said guide members and said inclined ledges causes the tubular rotator to turn until the outwardly extending stop members of the plunger slip off a set of ledges arranged on an upper part of the tubular rotator and thereby moving the plunger downward due to the force of an injection spring.

14. The medicament injection device according to claim 13,
wherein said tubular rotator comprises recesses in the outer surface configured to receive the guide members of the needle shield when during an outward movement of said needle shield,
the guide members of the needle shield move along the other side of said longitudinally extending ridges.

15. The medicament injection device according to claim 11,
wherein said plurality of ledges arranged on the inner surface of the upper part of the tubular rotator are configured such that the outwardly extending stop members of said plunger abut said ledges in a primed state of said medicament injection device.

16. The medicament injection device according to claim 1,
wherein said tubular rotator further comprises an outwardly extending knob being arranged to be contactable with an inwardly extending knob of said needle shield in an initial state of said medicament injection device.

17. The medicament injection device according to claim 16,
wherein said outwardly extending knob is arranged to be moveable out of contact with said inwardly extending knob of said needle shield when said injection device is brought into a primed state.

18. The medicament injection device according to claim 1,
wherein at least one of the plurality of ridges and of the plurality of protrusions provides a guide surface along which a guide member of said guide members runs during movement of said needle shield,
the guide surface having an inclination in relation to the longitudinal direction of the medicament injection device causing the tubular rotator to rotate somewhat in relation to the needle shield.

* * * * *